United States Patent [19]
Young et al.

[11] Patent Number: 6,048,514
[45] Date of Patent: Apr. 11, 2000

[54] AMYLIN ACTIVITY ASSAYS

[75] Inventors: Andrew A. Young, San Diego; Garth J. S. Cooper, Solana Beach; Timothy J. Rink, La Jolla, all of Calif.

[73] Assignee: Amylin Pharmaceuticals, Inc., San Diego, Calif.

[21] Appl. No.: 08/422,747

[22] Filed: Apr. 14, 1995

Related U.S. Application Data

[63] Continuation of application No. 08/088,629, Jul. 6, 1993, abandoned, which is a continuation of application No. 07/666,527, Mar. 8, 1991, abandoned, which is a continuation-in-part of application No. 07/640,478, Jan. 10, 1991, Pat. No. 5,234,906.

[51] Int. Cl.[7] .......................... A61K 38/22; A61K 49/00; G01N 33/15
[52] U.S. Cl. ............................... 424/9.2; 514/12; 514/21; 514/866; 514/884
[58] Field of Search ...................... 530/303, 304, 530/305, 350; 514/3, 4, 12, 21, 808, 866, 884; 435/7, 21, 7.8, 967; 436/501, 503, 86, 129; 424/9.1, 9.2

[56] References Cited

U.S. PATENT DOCUMENTS

| | | | |
|---|---|---|---|
| 4,521,430 | 6/1985 | Oh-ishi et al. | 514/211 |
| 5,234,906 | 8/1993 | Young et al. | 514/12 |
| 5,260,275 | 11/1993 | Cooper et al. | 514/13 |
| 5,280,014 | 1/1994 | Cooper et al. | 514/12 |
| 5,281,581 | 1/1994 | Cooper et al. | 514/12 |
| 5,321,008 | 6/1994 | Beaumont et al. | 514/12 |
| 5,376,638 | 12/1994 | Young et al. | 514/13 |

OTHER PUBLICATIONS

Cooper et al., 1014 Bioc. Biop. Acta 247, 1989.
Leighton et al., Diab. Med. 6:Suppl. 2,A14 (1989).
Leighton and Cooper, 335 Nature 632, 1988.
Ciaraldi et al., Diabetes 39:149A (1990).
Kruetter et al., Diabetes 39:121A (1990).
Koopmans et al., Diabetes 39:101A (1990).
Young et al., Diabetes 39:116A (1990).
V. Marks, "Glucagon in the Diagnosis and Treatment of Hypoglycemia," Chapter 55 of Handbook of Experimental Pharmacology, vol. 66/II, P.J. Lefebvre (ed.) 1983.
Young et al., Am. J. Physiol. 259:E457–61 (1990).
Leighton et al., TIBS 15:295–99 (1990).
Ahren et al., Int'l. Journal of Pancreatology 6:1–15 (1990).
Nishi et al., Journal of Biological CLemistry 265:4173–76 (1990).
Clark, Diab. Med. 6:561–67 (1989).
Cooper et al., Diabetes 1988, pp. 493–496, Larkins, Zimmet, and Chisholm (Eds.), (Elsevier Science Publishers B.V. 1989).
Cooper et al., Progress in Growth Factor Research 1:99–105 (1989).

(List continued on next page.)

*Primary Examiner*—Jeffrey E. Russel
*Attorney, Agent, or Firm*—Lyon & Lyon LLP

[57] ABSTRACT

Novel methods for use in identifying or assaying compounds which can simulate the ability of amylin to cause hyperlactemia and hyperglycemia in in vivo biological models, or for use in evaluating the potency of compounds known or suspected to simulate these actions of amylin, which involve introducing test samples into in vivo test systems and determining the presence or amount of a rise in lactate, or determining the presence or amount of a rise in lactate and a rise in glucose, following test sample administration.

12 Claims, 15 Drawing Sheets

OTHER PUBLICATIONS

Johnson et al., New England Journal of Medicine 321:513–18 (1989).

Leighton et al, "Reeffects of amylin on carbohydrate metabolism in skeletal muscle. . .". *Biochem. J.*, vol. 269. 1990 pp. 19–23.

Mitsukawa et al, "Islet Amyloid Polypeptide Response to Glucose, Insulin. . .". *Diabetes*, vol. 39, May 1990. pp. 639–642.

Molina et al, "Induction of Insulin Resistance In Vivo by Amylin and CGRP:1" *Diabetes*, vol. 39, Feb. 1990. pp. 260–265.

Yamaguchi et al,"CGRP and Induction of Hyperglycemia in Consious Rats In Vivo." *Diabetes*, vol. 39, Feb. 1990. pp. 168–174.

*Goodman and Gilman's The Pharmacological Basis of Therapeutics*, 8 ed. Pergamon Press 1990 pp. 63–64.

*The Merck Manual*, $14^{th}$ . ed. 1982 pp. 2284, 2298–2899.

Butter et al., "Effects of Meal Ingestion on Plasma Amylin Concentration. . .". *Diabetes*, vol. 39, Jun. 1990. pp. 752–756.

Cooper et al., "Amylin found in amyloid deposits in human type 2 diabetes mellitus. . .". *PNAS* vol. 85, Oct. 1988. pp. 7763–7766.

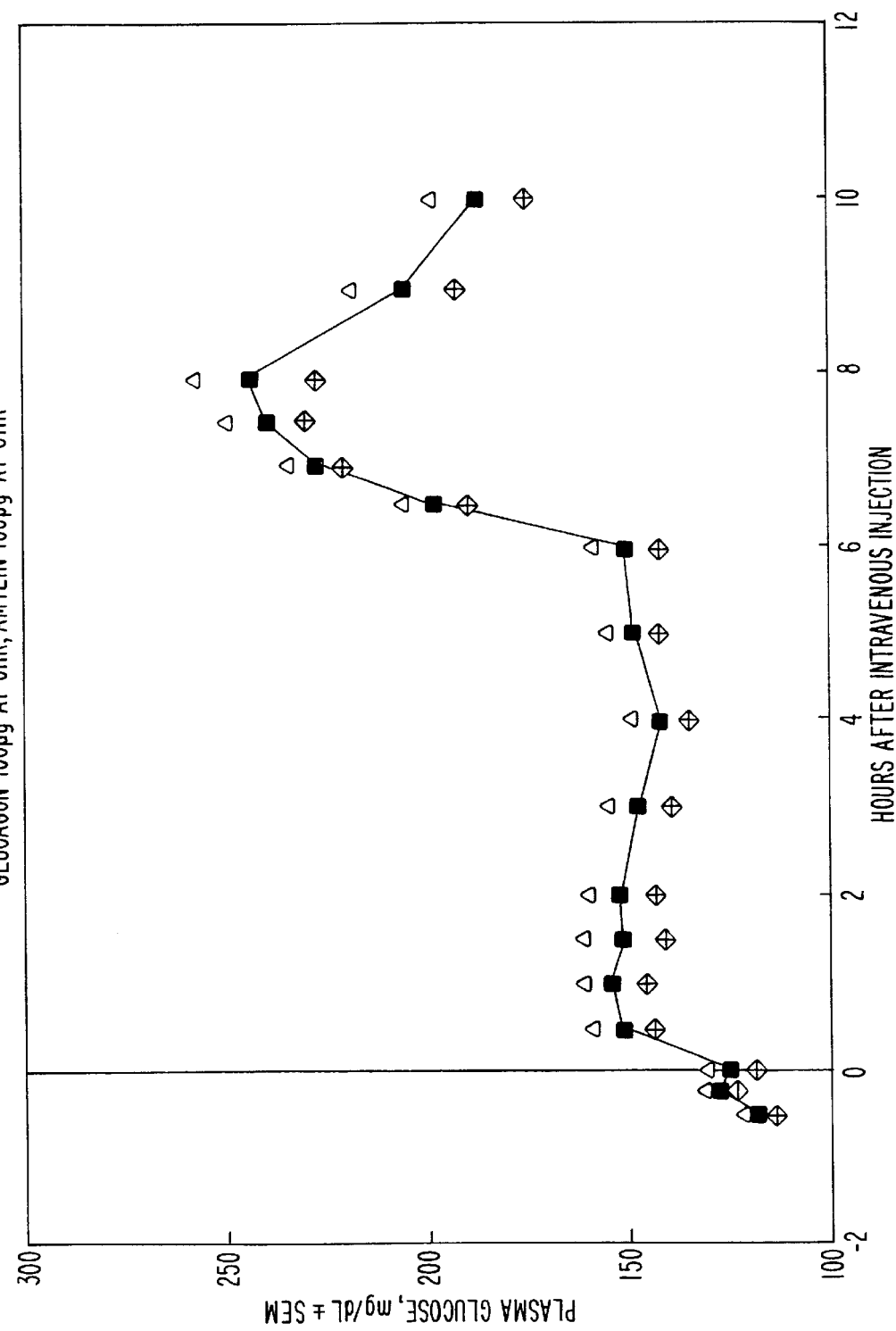

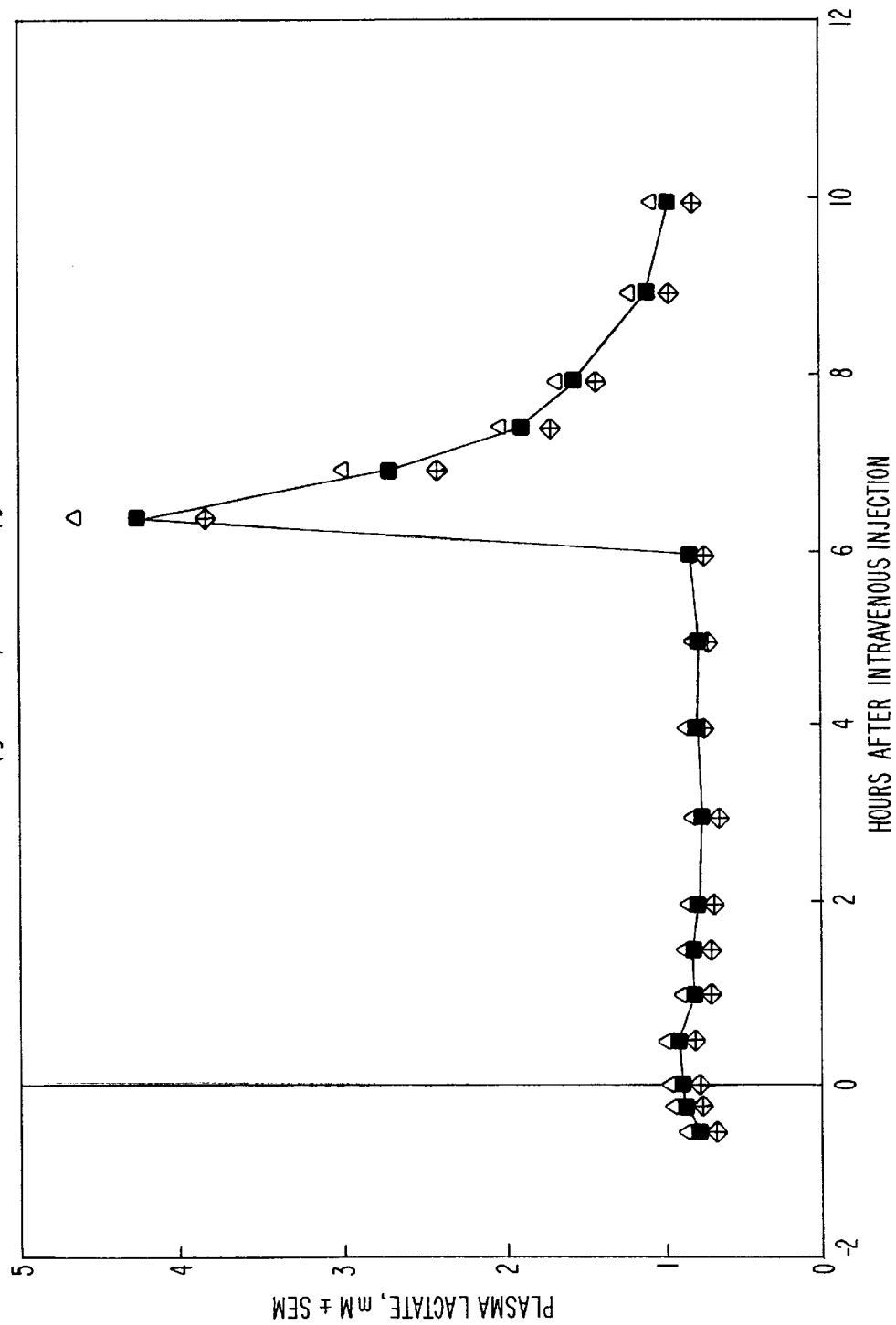

AMYLIN ACTIVITY ASSAYS

RELATED APPLICATIONS

This application is a continuation of U.S. application Ser. No. 08/088,629, filed Jul. 6, 1993, now abandoned, which application is a continuation of U.S. application Ser. No. 07/666,527, filed Mar. 8, 1991, now abandoned, which application is a continuation-in-part of U.S. application Ser. No. 07/640,478, filed Jan. 10, 1991, now U.S. Pat. No. 5,234,906, the contents of which are incorporated herein by this reference in their entireties.

FIELD OF THE INVENTION

The present invention involves the science of glucose metabolism and relates to hormone activity assays and uses for such assays. More particularly, the invention concerns amylin activity assays and their use in novel bioassay systems for the identification, characterization and evaluation of substances which function as agonists or antagonists of amylin action.

BACKGROUND AND INTRODUCTION TO THE INVENTION

All metabolic pathways must be regulated in order to serve the needs of individual cells, organs, or the whole body. Regulation of the metabolic pathways that provide fuel molecules, for example, carbohydrates, is essential if the supply is to be maintained in the various nutritional, metabolic, and pathologic conditions that are encountered in vivo. Metabolic fuel regulation involves provision of the specific fuel needs of each tissue, including making alternative fuels available. It also involves the transport of various involved substrates throughout the body, together with mechanisms to control their concentration in the blood.

These mechanisms ensure a continuous supply of glucose between meals and during a fast. Many conditions, typically associated with an enzyme deficiency, result in low blood glucose (hypoglycemia). Other, pathologic enzyme deficiencies can cause different but equally serious changes in carbohydrate metabolism, for example, insulin deficiency, which results in diabetes mellitus and increased blood glucose (hyperglycemia).

Glucose is know to be the primary currency of metabolic energy, and it circulates in the bloodstream to all the tissues and organs in the body. In the resting state humans typically utilize about 10 grams of glucose per hour, sixty percent of which goes to the brain. In the active state, the brain continues to draw about six grams of glucose per hour, but muscle use of glucose jumps to as much as forty grams per hour.

At mealtime, the consumption of food followed by its metabolism results in an infusion of glucose into the circulation at a rate greater than that required by the brain and other organs and tissues. To prevent an unacceptable rise in blood glucose level, i.e., hyperglycemia, glucose is extracted from circulation and stored as glycogen, principally in muscle tissue. The resulting process, which is regulated by insulin, is termed "insulin-stimulated glucose uptake."

In response to rising blood glucose levels and other stimuli related to food consumption, insulin is secreted by the pancreas into the bloodstream. Insulin is a protein hormone produced by the beta cells of the pancreatic Islets of Langerhans. Insulin decreases blood glucose in two ways. First, it signals muscle and fat tissues (so-called "peripheral" tissues) to increase glucose uptake for storage, respectively, as glycogen and fat. Second, insulin signals the liver to reduce glucose secretion.

During exercise, muscle demand for energy increases dramatically. Initially, muscles draw on their internal glycogen stores until this supply of glucose is exhausted. Glucose is also released into circulation by the liver as needed by the brain and non-muscle tissues. The process of drawing on liver glucose stores, which is also mediated by the pancreas, is termed "glucagon-stimulated glucose secretion".

In response to falling blood glucose levels related to vigorous activity, glucagon is secreted by the pancreas into the bloodstream. Glucagon is a polypeptide hormone produced by the alpha cells of the Islets of Langerhans in the pancreas. Glucagon increases blood glucose principally by stimulating glycogen breakdown to glucose, and subsequent secretion of that glucose, by the liver. It will be understood, then, that a major function of the liver is to maintain a relatively constant level of glucose in the blood.

The processes of carbohydrate metabolism include the pathways of glycolysis (under both aerobic and anaerobic conditions), oxidation of pyruvate to acetyl-CoA, glycogen biosynthesis in both muscle and liver, glycogen degradation in both muscle and liver, gluconeogenic pathways in both liver and kidney, the pentose phosphate pathway, the uronic acid pathway, and pathways relating to the metabolism of fructose, sorbitol (polyol), galactose, and amino sugars (hexosamines). There are dozens of enzymes implicated in some of these pathways, and such enzymes include glucokinase, the glycogen synthase system enzymes, phosphofructo-kinase-1, pyruvate kinase, and pyruvate dehydrogenase (enzymes of glycolysis and glycogenesis), pyruvate carboxylase, phosphoenolpyruvate carboxykinase, fructose-1,6-biphosphatase, and glucose-6-phosphatase (enzymes of gluconeogenesis), and glucose-6-phosphate dehydrogenase, 6-phosphogluconate dehydrogenase, malic enzyme, ATP-citrate lyase, acetyl-CoA carboxylase, and fatty acid synthase (enzymes of the pentose phosphate pathway and lipogenesis).

To this day, however, many underlying mechanisms of fuel metabolism remain confusing and the subject of academic controversy. Over the years, for example, views on whole-body glucose metabolism and the mechanisms of repletion of liver glycogen during the fasted-to-fed transition have continued to shift. McGarry, J. D., et al., *Ann. Rev. Nutr.* 7:51–73 (1987). As described herein, identification by Cooper of a third pancreatic hormone, amylin, has added a further factor to the already complicated fuel metabolism picture, and has necessitated a reevaluation of both fuel pathways and fuel pathway mechanisms. Eg., Cooper, G. J. S., et al., *Biochim. Biophys. Acta* 1014:247–252 (1989). Certain of these mechanisms, however, are well established.

Glycogen is understood to be an important factor in the generation and storage of metabolic energy, it being a readily mobilized storage form of glucose. Glycogen is a very large, branched polymer of glucose residues, most of which are linked by $\alpha$-1,4-glycosidic bonds. The branches are created by an $\alpha$-1,6 linkage between two glucose units. The two major sites of glycogen storage are the liver and skeletal muscle. The concentration of glycogen is higher in the liver, but more total glycogen is stored in skeletal muscle because of its greater mass.

As indicated, the synthesis and degradation of glycogen are important because they are used by the body to regulate the blood glucose level, glycogen providing a reservoir of glucose for use during strenuous muscle activity. The function of muscle glycogen is primarily to act as a readily available source of hexose units for glycolysis within the muscle itself. Liver glycogen is largely concerned with the export of hexose units for the maintenance of blood glucose levels, particularly between meals. It is known that glycogen synthesis and degradation occur through distinct reaction pathways. As in many other biological systems, the enzymes of glycogen metabolism are regulated by reversible phosphorylation.

FIG. 1 shows that regulation of glycogen metabolism is effected by a balance in activities between glycogen synthase and glycogen phosphorylase, which are under substrate control (through allostery) as well as hormonal control. Skeletal muscle phosphorylase exists in two interconvertible forms. Phosphorylase a is active and phosphorylase b is normally less active. Phosphorylase b is converted to phosphorylase a by phosphorylation of a serine residue in each of two subunits of the molecule. Hormones such as epinephrine and glucagon bind to receptors in the plasma membrane of target cells and trigger the activation of adenylate cyclase. Adenylate cyclase in the plasma membrane catalyzes the formation of cyclic AMP from ATP. The increased intracellular level of cyclic AMP activates a protein kinase, which is inactive in the absence of cyclic AMP. The protein kinase phosphorylates both phosphorylase kinase and glycogen synthase. The phosphorylation of these enzymes is the basis for coordinated regulation of glycogen synthesis and breakdown.

Glycogenolysis can be terminated and glycogenesis can be stimulated synchronously, or vice versa, because both processes are keyed to the activity of cAMP-dependent protein kinase. Both phosphorylase kinase and glycogen synthase may be reversibly phosphorylated in more than one site by separate kinases and phosphatases. These secondary phosphorylations modify the sensitivity of the primary sites to phosphorylation and dephosphorylation. Phosphorylation by the cyclic-AMP-dependent protein kinase switches on phosphorylase (by activating phosphorylase kinase) and simultaneously switches off glycogen synthase (directly) by converting it to its inactive form. Thus, inhibition of glycogen breakdown (glycogenolysis) enhances net glycogen synthesis (glycogenesis), and inhibition of glycogenesis enhances net glycogenolysis. Of further significance in the regulation of glycogen metabolism is the finding that the dephosphorylation of phosphorylase a, phosphorylase kinase, and glycogen synthase b (D-form) is accomplished by a single enzyme of wide specificity known as protein phosphatase-1. In turn, protein phosphatase-1 is inhibited by cAMP-dependent protein kinase via inhibitor-1. FIG. 1 also shows the control of glycogenolysis and glycogenesis by cAMP-dependent protein kinase. The reactions that lead to glycogenolysis as a result of an increase in cAMP concentrations include the conversion of glycogen synthase a to glycogen synthase b, the conversion of phosphorylase kinase b to phosphorylase kinase a, and the conversion of glycogen phosphorylase b to glycogen phosphorylase a. Concomitantly, the opposite conversions are inhibited under these conditions. The reverse occurs when cAMP concentrations decrease as a result of phosphodiesterase activity, leading to glycogenesis. For a discussion of carbohydrate fuel metabolism including glycolysis, gluconeogenesis, glycogenolysis and glycogen synthesis, see, e.g., McGarry, J. D., et al., supra; L. Stryer, *Biochemistry* (3d Edition 1988).

In 1929 Cori and Cori proposed that glucose carbons could be cycled in mammals through the sequence: liver glycogen→blood glucose→muscle glycogen→blood lactic acid→liver glycogen. Cori, C. F. and Cori, G. T., *J. Biol. Chem.* 81:389–403 (1929). For its part, muscle glycogen catabolism proceeds as follows. Glycogen is cleaved in the presence of glycogen phosphorylase a and orthophosphate to yield a phosphorylated sugar, glucose-1-phosphate. The enzyme glycogen phosphorylase a facilitates the sequential removal of glycosyl residues from the nonreducing end of the glycogen molecule, in which the glycosidic linkage between C-1 of the terminal residue and C-4 of the adjacent residue is split. The glucose 1-phosphate formed in the phosphorolytic cleavage of glycogen is converted into glucose 6-phosphate by another enzyme, phosphoglucomutase.

FIG. 2 shows the key enzymes in the control of glycolysis, gluconeogenesis, and glycogen metabolism in liver and muscle, the major differences in the muscle and liver pathways being that muscle is not affected by glucagon and does not contain the enzyme glucose-6-phosphatase, both of which are part of the liver pathways where indicated in the Figure. Glucose 6-phosphatase is a hydrolytic enzyme that enables glucose to leave the liver. It catalyzes the formation of glucose from glucose-6-phosphate, whereupon glucose can exit the liver cell via glucose transporters. Glucose-6-phosphate cannot be transported. The glucose-6-phosphatase enzyme is absent from the brain as well as muscle. The net result is that glucose 6-phosphate is retained by muscle and brain, which need large amounts of this fuel for the generation of ATP. By contrast, glucose is not a major fuel for the liver, an "altruistic" organ which stores and releases glucose primarily for the benefit of other tissues.

Glycogen metabolism is profoundly affected by specific hormones. While the mechanism of insulin action is not yet fully understood, insulin is known to increase the capacity of the liver to synthesize glycogen. Insulin also accelerates glycolysis in the liver, which in turn increases the synthesis of fatty acids. Whether liver glycolysis is the major or predominant source of pyruvate for fatty acid synthesis, however, has not been established. The entry of glucose into muscle and adipose cells is also promoted by insulin. The hormones epinephrine and glucagon have certain effects that counteract those of insulin. Muscular activity or the anticipation of muscular activity leads to the release of epinephrine from the adrenal medulla. Epinephrine markedly stimulates glycogen breakdown in muscle and, to a lesser extent, in liver. Another action of this catecholamine hormone is to inhibit the uptake of glucose by muscle. Instead, fatty acids released from adipose tissue are used as fuel. Epinephrine also increases the amount of glucose released into the blood by the liver and decreases the utilization of glucose by muscle by, respectively, stimulating the secretion of glucagon and inhibiting the secretion of insulin.

As noted above, the liver is responsive to glucagon, a polypeptide hormone that is secreted by the a cells of the pancreas when the blood sugar level is low. Glucagon increases the blood sugar level by stimulating the breakdown of glycogen in the liver and at the same time inhibiting glycogen synthesis. The net result of these actions is to markedly increase the output of liver glucose.

A newly discovered pancreatic hormone, amylin, is expressed mainly in pancreatic β cells and co-secreted with insulin. Amylin was first discovered as the major protein constituent of the islet amyloid which is found in patients with type 2 diabetes mellitus. E.g. Cooper, G. J. S., et al., *Proc. Nat. Acad. Sci. USA* 84–8628:8632 (1987); Cooper, G. J. S., et al, *Biochim. Byophys. Acta* 1014:247–252 (1989). Human amylin has a somewhat unusual amino acid composition in that it contains no acidic residues. Amylin is a 37 amino acid peptide having two post translational modifications, a $Cys^2$–$Cys^7$ intramolecular disulfide bond and a carboxy-terminal amide group. It was also discovered by Cooper that the presence of both of these post-translational modifications in the peptide structure of the synthetic molecule yield the greatest biological activity. E.g. Cooper, G. J. S., et al., *Proc. Natl. Acad. Sci. U.S.A.* 84:8628–8632 (1987); Cooper, G. J. S., et al. in *Diabetes* 1988, ed. Larkins, R., Zimmet, P. & Chisholm, D. (Elsevier, Amsterdam), pp. 493–496 (1989).

Human amylin has 43–46% sequence identity with human CGRP-1 and CGRP-2 (calcitonin gene-related peptides 1 and 2, respectively). Human amylin also has weaker sequence similarities with insulin, the relaxins, and the insulin-like growth factors (IGFs). This observation concerning sequence similarities supports the determination that there is a peptide hormone superfamily which includes the CGRPs, amylin, and the A-chain related region of the relaxins, insulin and the IGFs. Cooper, G. J. S., et al., *Progress in Growth Factor Research* 1:99–105 (1989).

Amylin is the product of a single gene present on chromosome 12 in humans. This gene has typical features of one encoding a polypeptide hormone, including prepro- and proamylin sequences, typical 5' and 3' dibasic processing signals, and a Gly residue 3' to the codon for the carboxy-terminal Tyr, which constitutes an amidation signal. Roberts, A. N., et al., *Proc. Nat. Acad. Sci. U.S.A.* 86:9662–9666 (1989). There is a high degree of interspecies conservation between both the amylins and the CGRPS, particularly in the region of the amino- and carboxy- termini. These regions of strong conservation correspond to the structural regions within the molecules which contain the post-translational modifications necessary for at least some of their biological activities. The variable sequence in the mid-portion of the amylin molecule contains the region said to be primarily responsible for amyloid formation.

Amylin is synthesized in the islets (Leffert, J. D., et al., *Proc. Natl. Acad. Sci. U.S.A.* 86:3127–3130 (1989) and Roberts, A. N., et al., *Proc. Natl. Acad. Sci. U.S.A.* 86:9662–9666 (1989)), from which it is secreted along with insulin in response to nutrient secretagogues. Ogawa, A., et al., *J. Clin. Invest.* 85:973–976 (1990). Amylin is packaged in the β-cell secretory granules, along with insulin. Experiments using an isolated perfused rat pancreas indicate that both glucose and arginine can stimulate amylin secretion in a biphasic pattern similar to that seen with insulin. Additionally, as with insulin, amylin secretion is amplified by combining the two secretagogues. Ogawa et al. *J. Clin. Inves.* 85:973–976 (1990); Fehmann et al., *FEBS Letters* 262:279–281 (1990). The amylin protein content within the pancreas has not been defined with certainty, although estimates using the rat pancreas as a model indicate the amylin mass to be about 4 to 6 times that of glucagon and 1 to 2 times of that of somatostatin.

Deposition of islet amyloid correlates well with the loss of islet β-cells and defective insulin secretion found in type 2 diabetics. Gepts, W., *The Islets of Lanaerhans*, ed. Cooperstein, S. J. & Watkins, D. (Academic Press, New York, N.Y.), pp. 321–356 (1980), Fehmann, H. C., et al., *FEBS Lett.* 262:279–281 (1990); Cooper, G. J. S., et al., *Biochim. Biophys. Acta* 1014:247–258 (1989). The ability of amylin to cause insulin resistance in many model systems, combined with its presence in human islet amyloid in diabetic pancreases supports the determination that it is central to the pathogenesis of non-insulin dependent diabetes mellitus. E.g. Cooper, G. J. S., et al., *Biochim. Biophys. Acta* 1014:247–258 (1989); Leighton, B. & Cooper, G. J. S., *Nature* (Lond) 335:632–635 (1988). Amylin also has been reported to produce marked effects on glucose metabolism in animals in vivo. In experiments utilizing the euglycemic, hyperinsulinemic glucose clamp, amylin reversed insulin-mediated suppression of hepatic glucose output in rats. Molina, J. M., Cooper, G. J. S., Leighton B. & Olefsky, J. M., *Diabetes* 39:260–265 (1990) and Koopmans, S. J., et al., *Diabetes* 39:101A (1990). Amylin also decreased peripheral uptake of glucose. Molina, J. M., Cooper, G. J. S., Leighton, B. & Olefsky, J. M., *Diabetes* 39:260–265 (1990); Koopmans, S. J., et al., *Diabetes* 39:101A (1990); Young, D. A., et al., *Diabetes* 39 (Suppl. 1):116A (1990).

Plasma lactate has long been known to be the principal three-carbon substrate for gluconeogenesis and for fatty acid synthesis. Other important three-carbon substrates include alanine and glycerol. As such, lactate is now considered by some to be a key link in the pathways that lead to storage of glycogen in liver and to storage of triglyceride in fat cells. Others have viewed lactate principally as an end-product of glycolysis, which supplies energy in the form of ATP under anaerobic conditions and distributes the metabolic load over both space and time. For example, Stryer, supra, identifies lactate as a dead end in metabolism, the only purpose of the reduction of pyruvate to lactate being to regenerate $NAD^+$ so that glycolysis can proceed in active skeletal muscle and erythrocytes. In other words, as described above with regard to the Cori cycle, the liver is believed to furnish glucose to the contracting skeletal muscle, which derives ATP from the glycolytic conversion of glucose into lactate, glucose then being synthesized from lactate by the liver.

The principal source of the lactate which enters the Cori Cycle has remained the subject of debate. While some indicate that the lactate originates from muscle in diabetic subjects (Capaldo, B., et al., *J. Clin. Endo. Metab.* 71:1220–1223 (1990)), others say that it comes from tissues other than muscle, such as fat. Jansson, P. A., et al., *Diaetalogia*, 33:253–256 (1990). Whatever its source, still another group also concluded that, while increased substrate delivery to the liver and increased efficiency of intrahepatic substrate conversion to glucose are both important factors for the increased gluconeogenesis characteristic of Type 2 diabetics, tissues other than muscle are responsible for the increased delivery of gluconeogenic precursors to the liver. Consoli et al., *J. Clin. Invest.* 86:2038–2045 (December 1990).

The role of amylin also remains the subject of debate. In skeletal muscle in vitro, amylin has been discussed in regard to or implicated in many different pathways of carbohydrate metabolism, including incorporation of glucose into glycogen (Leighton, B. & Cooper, G. J. S., *Nature* 335:632–635 (1988); Cooper, G. J. S., et al., *Proc. Natl. Acad. Sci. U.S.A.* 85:7763–7766 (1988); Leighton, B., and Foot, E., *Biochem J.* 269:19–23 (1990)), glycogenolysis (Young et al., *Am J. Physiol.* 259:457–461 (1990); Leighton, B., Foot, E. A. & Cooper, G. J. S. (1989) *Diab. Med.* 6: Suppl. 2, A4 (1989)), glycogenesis (Young et al., supra), and glucose uptake (Young et al., supra; Ciaraldi, T. P., Cooper, G. J. S. & Stolpe, M., *Diabetes* 39, 149A (1990); Kreutter, D. et al., *Diabetes* 39, (Suppl. 1) :121A (1990); Leighton, B., et al., *FEBS Letters* 249:357–361 (1989)). The effects of amylin in skeletal muscle depend upon distribution of fiber type. Leighton, B., Foot, E. A. & Cooper, G. J. S. (1989) *Diab. Med.* 6 (Supp. 2):A4 (1989). While amylin was reported to inhibit glycogen synthesis in both red (soleus) and white (extensor digitorum longus) muscle in vitro, it was reported to stimulate glycogenolysis (and subsequent lactate production) only in white muscle. Id. White (type II) muscle fibers constitute the bulk of muscle mass in most mammals surveyed. Ariano, M. A., et al., *J. Histochem. Cytochem.*

21:51–55 (1973). The effects of amylin on glycogen synthesis in isolated red muscle (soleus) were reported equipotent with those of the pure β-adrenergic agonist, isoprenaline. Leighton, B. & Cooper, G. J. S., *Nature* (Lond) 335:632–635 (1988). In L6 myocytes, maximal reduction of glucose uptake has been reported at 10 pM. Ciaraldi, T. P., Cooper, G. J. S., & Stolpe, M., *Diabetes* 39:149A (1990); Kreutter, D., et al., *Diabetes* 39 (Suppl. 1):121A (1990).

Amylin Corporation's International Patent Application No. PCT/US89/00049, "Treatment of Type 2 Diabetes Mellitus" was published on Jul. 13, 1989, bearing International Publication Number WO 89/06135. The inventions described therein by Cooper and Greene include compounds and methods for blocking or mitigating the effects of amylin, which enables, for example, the treatment of type 2 diabetics. Type 2 diabetes is characterized by insulin resistance, which may be defined as a failure of the normal metabolic response of peripheral tissues to the action of insulin. In clinical terms, insulin resistance is present when normal or elevated blood glucose levels persist in the face of normal or elevated levels of insulin. It represents, in essence, a glycogen synthesis inhibition, by which either basal or insulin-stimulated glycogen synthesis, or both, are reduced below normal levels.

Application PCT/US89/00049 describes and claims means to accomplish amylin regulation, for example, by blocking the binding of amylin, calcitonin gene related peptide (CGRP), and other amylin agonists by the use of competitive inhibitors including substituted or altered peptides or subpeptides of amylin or CGRP, or by regulation of the expression or production or release of amylin or CGRP. Chemical antagonists to amylin which bind to the amylin receptor without triggering a response are used to reduce the effects of amylin or amylin agonists which act to inhibit the body's basal and insulin-stimulated responses to glucose, or to prevent the interference of those molecules with insulin release.

The application also sets forth methods for identifying additional compounds having utility for the treatment of type 2 diabetes. In this regard, the application describes the use of biological screening for synthetic or other amylin antagonists. For example, a potential or suspected antagonist is added to isolated muscle or muscle cells together with purified amylin, in the presence or absence of insulin, and glucose uptake by cells in the tissue culture is monitored. An increase in the uptake in the presence of a potential or suspected antagonist is relied upon to indicate that the compound had the required inhibitory properties. The application also discloses the use of isolated hepatocytes, islets of Langerhans or isolated islet B cells in a similar protocol in which increased insulin output is monitored instead. The application also discloses immunoassay-type screening in which the ability of test samples containing one or more synthetic or other compounds to displace amylin or anti-idiotype antibodies from monoclonal antibodies immobilized in microtitre plates is used to screen for materials which should be further evaluated under the biological testing parameters noted above.

Of great utility would be a further functional assay system or systems in which a potential or suspected agonist or antagonist of amylin could not only be identified, but characterized and specifically evaluated based upon its ability to stimulate or inhibit amylin activity at its major site or sites of action and independent of another modulator of cell action, that is, without needing to measure inhibition of an insulin-stimulated process. This site of action has now been discovered, and such novel assay systems has been invented and are described and claimed herein.

Other surprising and important aspects of amylin action in vivo on carbohydrate metabolism have also now been discovered and are described herein as the basis of further novel assay systems. First, as set forth in the below Examples, we have discovered that amylin acts primarily in vivo to increase plasma lactate levels, not glucose levels as originally believed, and in fasted animals that the increased lactate then results in sharply increased plasma glucose levels. More specifically, in lightly anesthetized rats which were fasted for 18 hours to deplete their stores of hepatic glycogen, amylin injections stimulated lactate production. These rises in plasma lactate were followed about 10 to 30 minutes later by increased plasma glucose levels. Importantly, these effects were observed for both intravenous and subcutaneous injections. The effects of amylin in fed rats differ from effects in fasted animals. In fed rats with presumably normal liver glycogen stores, amylin causes the same marked rise in plasma lactate; however, this lactate rise is followed by only a modest or no rise in plasma glucose. Glucagon is also known to increase plasma glucose, as described above, an action which reflects the important counterregulatory role of glucagon in preventing hypoglycemia. In both fasted and fed rats, however, while amylin produces a sharp increase in plasma lactate, glucagon exerted no effect on plasma lactate levels. Amylin was also discovered to cause greater increases in plasma glucose than glucagon in fasted rats, while these relative activities are reversed in fed rats.

We have discovered that amylin is an anabolic hormonal partner for insulin. Amylin directly stimulates the supply of 3-carbon substrate for gluconeogenesis, a principle avenue to hepatic glycogen synthesis, and in a dose-dependent fashion. Amylin also reduces skeletal muscle insulin sensitivity without affecting insulin-stimulated glucose uptake in fat cells, and increases the supply of 3-carbon substrates for fatty acid synthesis in the liver. These discoveries provide a basis for additional assay systems which evaluate the ability of a known or suspected agonist or antagonist of amylin function to affect amylin action, and to generate dose response profiles for said known or suspected agonists or antagonists which may then, optionally, be contrasted with dose response profiles prepared in positive and/or negative control assays.

SUMMARY OF THE INVENTION

The invention provides methods for identification, characterization and evaluation of test samples containing one or more test compounds for their ability to regulate the effects of amylin, a hormone which has been isolated and purified from the pancreatic amyloid masses typically found in type 2 diabetics, and which is responsible in both physiologic as well as certain pathologic conditions for the regulation of the Cori cycle in glucose metabolism, among other things. Specifically, the invention provides methods for identifying, characterizing and evaluating the effect of compounds on the ability of amylin, or amylin agonists such as CGRP, to ultimately enhance the activity of glycogen phosphorylase a in appropriate cell-based systems. In such a system, amylin-sensitive cells that utilize glycogen as a form of carbohydrate storage are incubated with a compound or compounds of interest, which may be a putative agonist or antagonist of amylin. Where the test compound is a putative amylin antagonist, amylin or an amylin agonist is then added to the cells. Subsequently the cells are evaluated after a predetermined time to determine, in one embodiment, the rate of phosphorylase a-catalyzed breakdown of glycogen. The invention also contemplates the optional use of control assays in which known agonists of amylin, such as CGRP or amylin itself, and/or known antagonists of amylin, such as $CGRP_{8-37}$, are utilized to provide positive and/or negative controls, or standards, for reference to the compound or compounds of interest. The amylin activation of the assay system can also be modulated by insulin, and it can be used to identify and evaluate agonists of insulin and, in a still further embodiment, to distinguish between antagonists of amylin and agonists of insulin.

One embodiment within the novel assay systems of this invention is a first assay method for use in identifying a test compound which can inhibit the activity of amylin, or for use in evaluating the potency of a test compound known to inhibit the activity of amylin, which includes bringing a test sample and an amylin-sensitive cell system, said test sample containing one or more test compounds, and said amylin-sensitive cell system comprising cells that can utilize glycogen as a form of carbohydrate storage and are sensitive to amylin as reflected by the ability of amylin or an amylin agonist to activate glycogen phosphorylase in said cells; incubating said amylin-sensitive cell system and said test sample for a predetermined period of time; adding a predetermined amount of amylin or amylin agonist to said test sample and said amylin-sensitive cell system; disrupting said cell system in order to expose the contents of cells in said cell system; assessing the activity of glycogen phosphorylase a; and, determining whether said test compound can inhibit, or measuring the ability of said test sample to inhibit, the activation of glycogen phosphorylase a by said amylin or amylin agonist. Determination of the ability of the test sample to inhibit the activation of glycogen phosphorylase a by amylin or an amylin agonist may be valued qualitatively, that is, a yes-no answer can be obtained. Measurement of the ability of a test sample to inhibit the activation of glycogen phosphorylase a by amylin or an amylin agonist can be either semiquantitative or quantitative. This assay method also may include the use of a positive control, a negative control, or both. Such a control assay or assays can be used to assist in determining or measuring the ability of a test compound or compounds to inhibit the activation of glycogen phosphorylase a by amylin or an amylin agonist. A negative control assay can be carried out by following the above first assay method, but without the addition of a test compound or test compounds. Where an amylin agonist is utilized in the above first assay method, or in a negative control assay carried out according to the above first assay method, said amylin agonist may comprise, for example, CGRP. A positive control assay may be carried out according to the above first method, wherein the test compound used is one that is known to inhibit amylin activation of glycogen phosphorylase, such as $CGRP_{8-37}$. These methods may be carried out in any number of cell-based systems, including isolated muscle tissue preparations such as the soleus muscle assay.

A further embodiment within the novel assay systems of this invention includes a second assay method for use in identifying a test compound which can act as an agonist of amylin, or for use in evaluating the potency of a test compound known to have amylin agonist activity, which method includes the steps of bringing together a test sample and an amylin-sensitive cell system, said test sample and said amylin-sensitive cell system being as described above; incubating said amylin-sensitive cell system and said test sample for a predetermined period of time; disrupting said cell system in order expose the contents of cells in said system; assessing the activity of glycogen phosphorylase a; and, determining whether said compound can stimulate, or measuring the ability of said test sample to stimulate, the activation of glycogen phosphorylase a. This method for identifying or evaluating agonists of amylin may also further include the use of a positive control, a negative control, or both. A negative control assay can be carried out as described for the above second assay method wherein the test compound or test compounds comprise an amylin antagonist, such as $CGRP_{8-37}$. A positive control assay can be carried out as described for the above second assay method, but using a test compound known to stimulate the amylin receptor-mediated activation of glycogen phosphorylase, such as CGRP.

Also contemplated by the present invention is a method for use in identifying a test compound which can act as an agonist of insulin, or for use in evaluating the potency of a test compound known to have insulin agonist activity, which includes the steps of bringing together a test sample and an insulin- and amylin-sensitive cell system, said test sample containing one or more test compounds, and said insulin- and amylin-sensitive cell system comprising cells that can utilize glycogen as a form of carbohydrate storage, are sensitive to amylin as reflected by the ability of amylin or an amylin agonist to activate glycogen phosphorylase in said cells, and are sensitive to insulin as reflected by the ability of insulin or an insulin agonist to inhibit activation of glycogen phosphorylase in said cells; incubating said amylin-sensitive cell system and said test sample for a predetermined period of time; disrupting said cell system in order to expose the contents of cells in said cell systems; assessing the activity of glycogen phosphorylase a; and determining or measuring the ability of said test sample to inhibit the activation of glycogen phosphorylase a. Examples of such a cell system include the isolated soleus muscle assay described herein.

In a still further aspect of the invention, the specificity of a test compound (as an agonist of insulin or an antagonist of amylin), which is determined or known to inhibit glycogen phosphorylase a activity can be assessed by bringing the test compound together with a second test system comprising cells that are sensitive to insulin but not amylin. Such a second test system includes fat cells in which insulin-mediated uptake of glucose can be experimentally evaluated.

A further assay method for use in identifying a test compound which can inhibit the activity of amylin, or for use in evaluating the potency of a test compound known to inhibit the activity of amylin, comprises bringing together a test sample and a test system, the test sample comprising one or more test compounds, and the test system comprising an in vivo biological model that exhibits elevated lactate output and elevated glucose levels in response to the introduction of amylin or an amylin agonist; adding a predetermined amount of amylin or amylin agonist to the test system; and determining the presence or amount of a rise in lactate in said test system. This method may further comprise determining the presence or amount of a rise in glucose in the test system. Optionally, the assay method may also include the use of a positive control assay, a negative control assay, or both. Dose response curves for both the lactate and glucose responses in the assay method, as well as the control assays, can be prepared and beneficially utilized in evaluating the amylin inhibition of any test compound or compounds. Exemplified in vivo systems include experimental animals, such as the rat.

A still further assay method for use in identifying a test compound which can simulate the activity of amylin, or for use in evaluating the potency of a test compound known to simulate the activity of amylin, is also disclosed which includes the steps of bringing together a test sample and a test system, said test sample comprising one or more test compounds, and said test system comprising an in vivo biological model that exhibits elevated lactate levels and elevated glucose levels in response to the introduction of amylin or an amylin agonist; and, determining the presence or amount of a rise in lactate in said test system, and optionally further determining the presence or amount of a rise in glucose in said test system. As with the immediately preceding method, positive control assays, negative control assays, or both may be utilized in evaluating the ability of the test compound to simulate amylin activity. Appropriate dose response curves reflecting effects on lactate and glucose for each of these assays and control assays can be generated which also aid in this evaluation.

In a further embodiment of the invention, an assay method for use in determining the amount of bioactive material in a test sample which is known or suspected to contain amylin or an amylin agonist is provided, which method includes the steps of bringing together a test sample to be assayed for amylin bioactivity and a test system, said test system comprising an in vivo biological model, said biological model exhibiting elevated lactate levels followed by elevated glucose levels in response to the introduction of amylin or an amylin agonist; determining the amount of arise in lactate levels; repeating the assay method using differing amounts of test sample and generating a dose response profile for the rise in lactate levels for use in measuring the amylin bioactivity of the test sample. Optionally, the method further includes steps of determining the amount of a rise in glucose in said test system; repeating the assay method using differing amounts of the test sample; and, generating a dose-response profile for said rise in glucose for use in measuring the amylin bioactivity of the test sample. This method may further include comparing the dose-response profile or profiles for said test sample to a dose response profile prepared for one or more positive control assays, or one or more negative control assays, or both, and measuring the amylin bioactivity of said test sample. This method may still further include comparing a dose-response profile or profiles generated for said test sample to a dose-response profile prepared for an amylin standard, a negative control standard, or both. The in vivo lactate and glucose response assays described and claimed herein exhibit unexpected and surprising reproducibility and precision.

Test samples used in all of the above methods that contain more than one test compound and which yield positive results can be then divided and retested as many times as necessary, and as appropriate, to identify the compound or compounds in said test sample containing more than one test compound which is responsible for yielding the positive result.

Amylin agonists useful in the disclosed and claimed assay methods also include [$Pro^{29}$]-human amylin, [$Leu^{23}$]-human amylin, and $cyclo^{2,7}$ [$Asp^2$, $Lys^7$]-human amylin.

BRIEF DESCRIPTION OF THE DRAWINGS

FIGS. 9A and 9B show the effects of an intravenous injection of 100 micrograms glucagon (0 hours) followed by an intravenous injection of 100 micrograms amylin (6 hours) on plasma arterial levels of glucose (9A) and lactate (9B) in 18-hour fasted rats.

DETAILED DESCRIPTION OF THE INVENTION

In vitro studies have shown that amylin can act on skeletal muscle to decrease rates of glucose uptake and incorporation into glycogen. It has been proposed that amylin, in in vitro studies, can increase gluconeogenesis, reduce glycogen content and increase lactate production. However, it has also been proposed that these proposals might be explained by inhibition of glycogen synthesis (Young et al., supra) and one recent report stated that amylin does not promote muscle glycogen breakdown or enhance lactate production in the presence of insulin. Leighton, B. and Foot, E., supra.

We have discovered, unexpectedly, that amylin stimulates hepatic glycogenolysis, gluconeogenesis, skeletal muscle glycogenolysis and inhibits insulin-mediated glycogen synthesis. Furthermore, we have now discovered that a major site of action of amylin in peripheral tissue is the stimulation of glycogen phosphorylase a activity. Glycogen phosphorylase catalyzes the breakdown of glycogen. Phosphorylase b is the inactive form of the enzyme, activated by lower ATP/high AMP or transientincreases in intracellular calcium as produced by muscular contraction. Phosphorylase a is the active form of the enzyme, and is active regardless of any of the above conditions. Until now, however, the only known activator of the phosphorylase b/phosphorylase a conversion has been adrenergic stimulation (epinephrine) which works via cAMP-dependent kinase. Insulin, importantly, appears not to inhibit this adrenergic conversion. Incubation of isolated rat soleus muscle in Krebs-Ringer-bicarbonate buffer containing amylin stimulates the muscle glycogen phosphorylase b/phosphorylase a conversion. This conversion takes place in the absence of insulin. However, in contrast to adrenergically-mediated activation of phosphorylase, the presence of insulin in the medium (1,000 μU/mL) markedly inhibits the amylin stimulation of phosphorylase activity.

Figure 1:
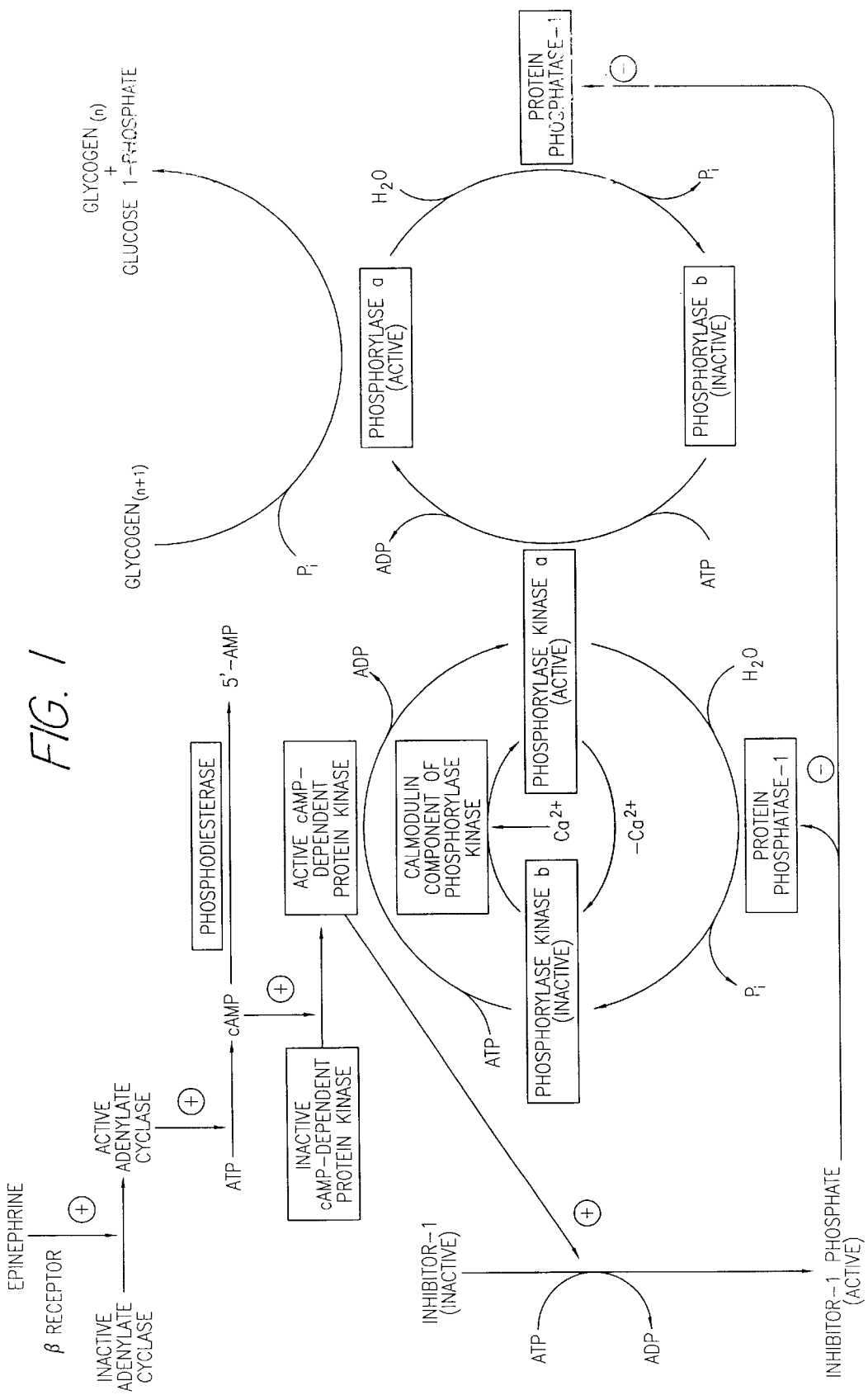
FIG. 1 shows certain catabolytic and anabolic pathways of glycogen metabolism in muscle and, specifically, the control of phosphorylase.
Figure 2:
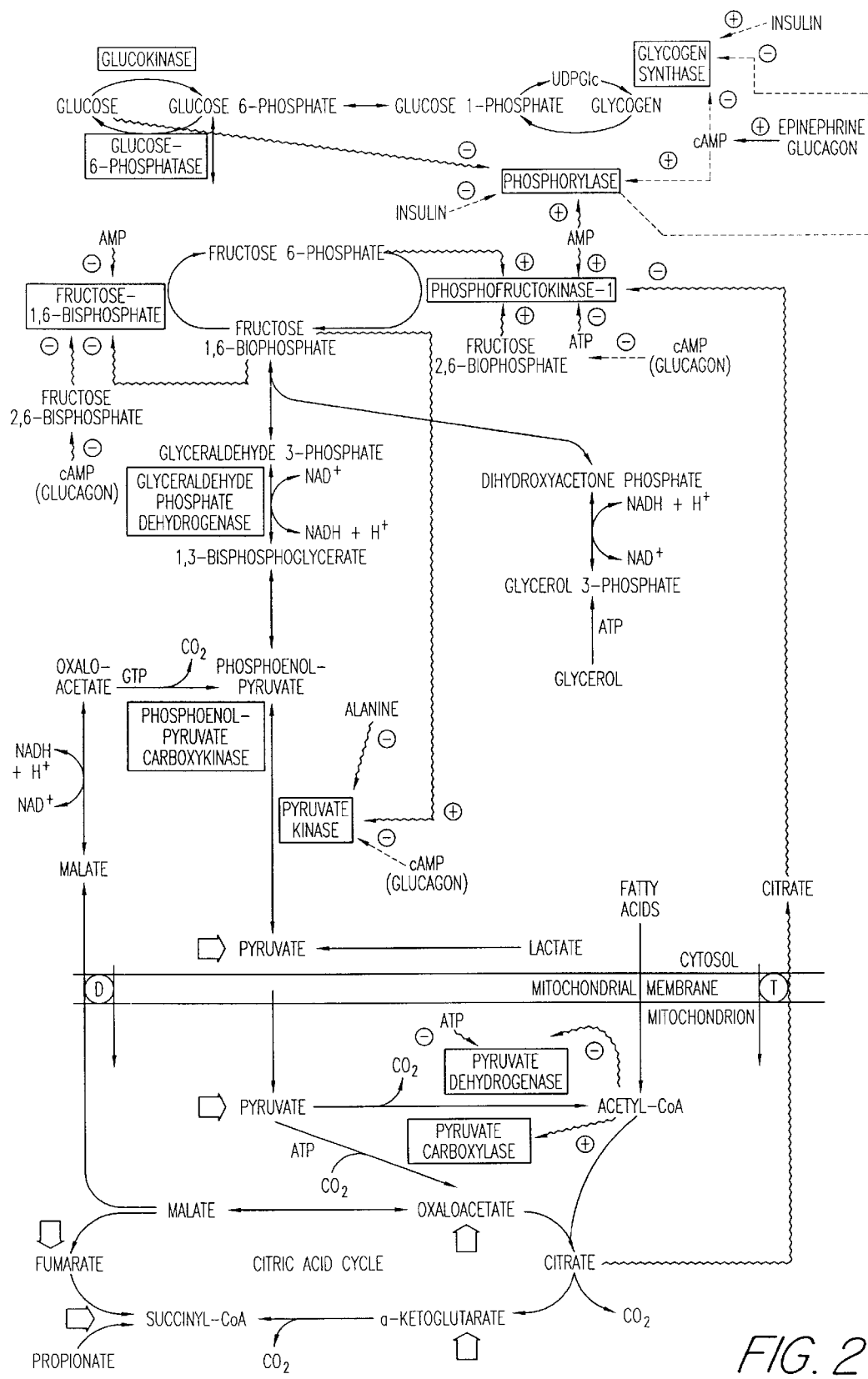
FIG. 2 shows various enzymes involved in the control of glycolysis, gluconeogenesis, and glycogen metabolism in liver and muscle. Activation and inhibition are indicated by pluses minuses, respectively. D represents the dicarboxylate transporter and T represents the tricarboxylate transporter.
Figure 3:
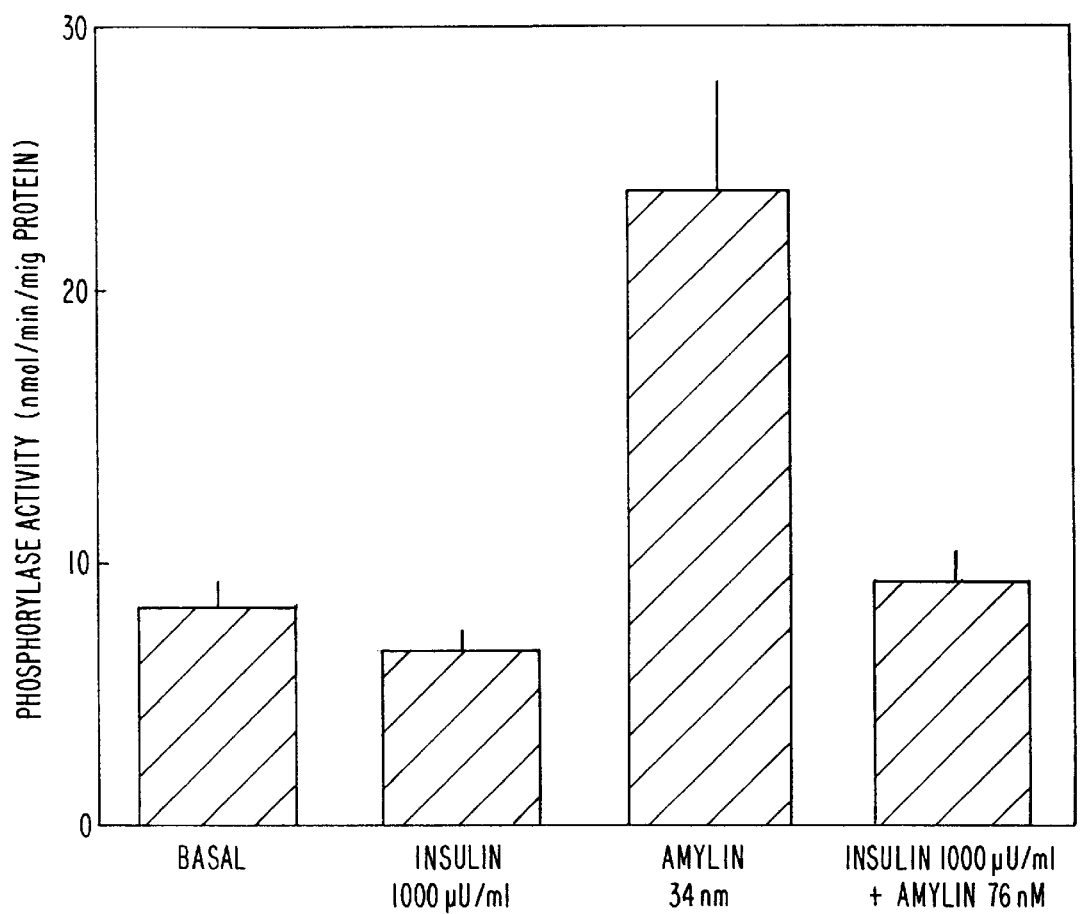
FIG. 3 shows glycogen phosphorylase activity in the presence of amylin and insulin. Glycogen phosphorylase a in the isolated soleus muscle after 1 hour incubation with insulin alone (7.1 nM), rat amylin alone, (34 nM) or insulin (7.1 nM) plus rat amylin (76 nM). Bars represent mean±SEM, n=4 at each point.
Figure 4:
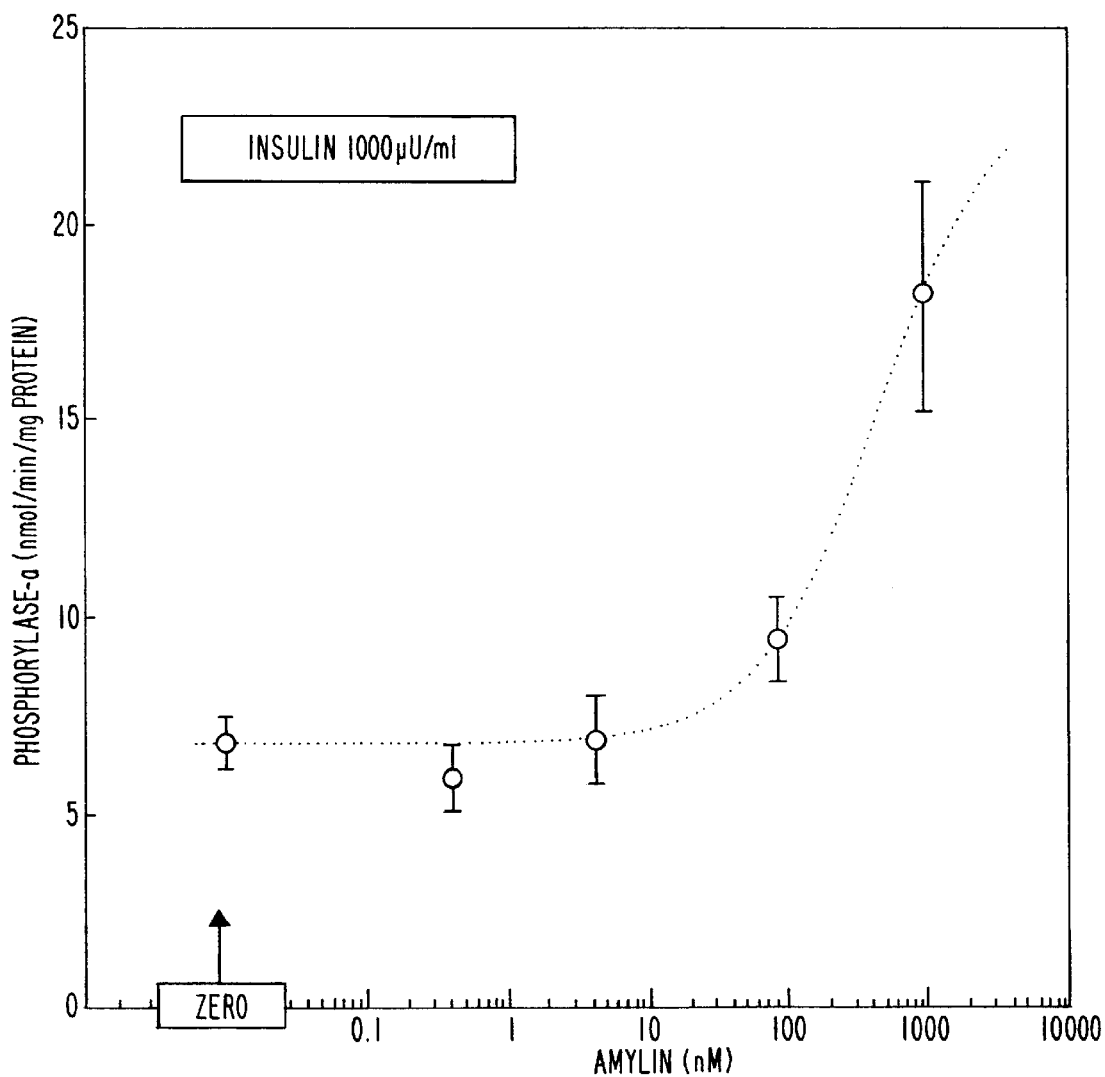
FIG. 4 shows a glycogen phosphorylase/amylin dose response. Glycogen phosphorylase a activity in the isolated soleus muscle following 1 hour incubation with increasing concentrations of amylin in the presence of 7.1 nM insulin. Bars represent means±SEM, n=4 at each point.

As shown in the below Example 1, we have demonstrated the ability of amylin to enhance glycogen breakdown by the indirect stimulation of glycogen phosphorylase a. Glycogen phosphorylase a activity was tested in extracts of powdered, frozen rat muscle as described. Results, which are shown in FIG. 3, demonstrate that treatment of isolated rat skeletal muscle with 34 nM amylin in the absence of insulin increase the activity of muscle glycogen phosphorylase a by 2.8 fold, from a basal level of 8.5±0.8 nmol/min/mg protein to 23.7±4.1 nmol/min/mg protein. Furthermore, amylin produced a dose-dependent increase in the activity of glycogen phosphorylase a in the presence of 7.1 nM insulin. See FIG. 4. Enzyme activity increased 2.7-fold from a basal level of 6.8±0.7 nmol/min/mg protein in the absence of amylin to 18.1±2.9 nmol/min/mg protein at an amylin concentration of 781 nM (P<0.0001).

In the absence of amylin, 7.1 nM insulin did not produce a significant change in glycogen phosphorylase a activity (Table 1). On the other hand, in the presence of amylin, insulin significantly decreased glycogen phosphorylase a activity. Thus, at 34 nM amylin in the absence of insulin, enzyme activity was 23.7±4.1 nmol/min/mg protein. At an insulin concentration of 7.1 nM, phosphorylase a activity in the presence of 76 nM amylin fell to 9.4±1.0 nmol/min/mg protein (P<0.02 compared with activity at 34 nM amylin alone).

This newly discovered activity of amylin can be made use of in a cell-based system to screen for and/or evaluate the activity of amylin agonists and antagonists. The reaction cascade $$\text{Glycogen}_{(n)} + P_i \rightarrow \text{Glycogen}_{(n-1)} + \text{Glucose-1-phosphate} \quad [1]$$

$$\text{Glucose-1-phosphate} \rightarrow \text{Glucose-6-phosphate} \quad [2]$$

$$\text{Glucose-6-phosphate} + \text{NADP}^+ \rightarrow \text{6-phosphoglucono-}\delta\text{-lactone} + \text{NADPH} + \text{H}^+ \quad [3]$$

results in the generation of NADPH, which is fluorescent. If ATP is added and calcium (Ca$^{2+}$) is kept low, ATP will inhibit phosphorylase b activity. Other enzymes are then added in sufficient quantity and, where sufficient NADP and P$_i$ are present, the reaction rate (determined by the rate of increase of NADPH-fluorescence) is limited by the amount of glycogen phosphorylase a present, that presence being a direct consequence of the prior incubation with amylin. Amylin agonists, as well as adrenergic agonists, will increase the reaction rate. Amylin antagonists will inhibit the reaction rate expected from subsequent application of amylin.

In one embodiment of this method, isolated mammalian skeletal muscle preparations are used as the assay system, as in the below Example 1. In another embodiment of this method, cultured amylin-sensitive cells which utilize glycogen as a form of carbohydrate storage and show at least about a 3-fold increase in phosphorylase activity on maximal stimulation by amylin are utilized. Preferred are myocyte (muscle) tissue or cell lines. Most preferred are skeletal muscle tissue or cell lines. Also preferred are muscle cell lines that retain muscle phenotypic properties. In a further embodiment of this method a muscle-like cell line is created by genetic engineering based on a method reported by Weitraub et al. (*Science* 251:761–766 (1991)) whereby the myoID gene can be transfected into, for example, fibroblast cell lines using an appropriate promoter construct, such as a viral LTR promoter. The cells are then elicited to differentiate into a skeletal muscle-like cell phenotype. The selected tissue preparation or cell line is then incubated for a predetermined time with a compound of interest, for example, a putative amylin agonist or putative amylin antagonist. Where the assay is being used to identify, evaluate or characterize a putative or known amylin antagonist, this compound is added about 10, 20, or 30 minutes prior to the addition of an amylin agonist to the cell culture, preferably to a final concentration that elicits at least about 75% of the maximal amylin response, the $EC_{75}$. The cells are disrupted, and ATP inorganic phosphate, phosphoglucose isomerase, glucose-6-phosphate dehydrogenase, and NADP are added to the mixture and incubated for about 5 minutes. Cells may be disrupted by methods known to those in the art, including physical means, such as sonication, and lysing compounds, such as detergents which break the cell membrane. Following this incubation, glycogen phosphorylase a activity may be measured using any of several known methods. In the method described herein, the change in NADPH fluorescence change over a fixed interval was used to determine the rate of phosphorylase a catalyzed glycogenolysis. Glycogen phosphorylase can be assayed in either the direction of glycogen phosphorolysis or in the direction of glycogen synthesis.

Thus, the activity of glycogen phosphorylase can also be determined from the reverse reaction:

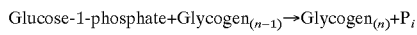

$$\text{Glucose-1-phosphate} + \text{Glycogen}_{(n-1)} \rightarrow \text{Glycogen}_{(n)} + P_i$$

Using the method described above, conditions can be altered to invoke zero-order kinetics so that enzyme activity can be determined by inference from the reaction rate. Glucose-1-phosphate can be radiolabelled using, for example, $C^{14}$ or $P^{32}$ and followed into either glycogen or inorganic phosphate, respectively. Gilboe, D. P., et al., *Analytical Biochemistry* 47:20–27 (1972).

Other methods for assessing glycogen phosphorylase activity can also be beneficially used in the described and claimed invention. Glycogen phosphorylase activity can be monitored by using differential spectropolarimetry, (Mason, M. and Fasella, P., *Analytical Biochemistry* 43:57–65 (1971)), by using a filter paper technique for the assay of phosphorylase in the direction of glycogen synthesis (Wang, P. and Esmann, V., *Analytical Biochemistry* 47:495–500 (1972)), by using a titrimetric assay to measure enzyme rate in either direction (Palter, K. and Lukton, A., *Analytical Biochemistry* 53:613–623 (1973)), by using a pH electrode assay to measure liberated phosphate (McCracken, D. A. and Rutherford, W. M., *Analytical Biochemistry*, 101:275–277 (1980)), by using a bioluminescent assay to measure NADPH formation (R. J. Hughes, *Analytical Biochemistry* 131:318–323 (1983)), and by using various spectrophotometric assays for inorganic phosphate (Bencini, D. A., et al. *Analytical Biochemistry* 132:254–258 (1983); Saheki, S., et al., *Analytical Biochemistry* 148:277–281 (1985)).

Numbers of samples can be processed simultaneously using various glycogen phosphorylase assays that include, for example, an instantaneous method of phosphate determination (Carney, I. T., et al., *Analytical Biochemistry* 85:321–324 (1978)), or by using an automated glycogen phosphorylase assay system (Haschke, R. H. and Heilmeyer, L. M. G., *Analytical Biochemistry* 47:451–456 (1972)).

We have also discovered that, unexpectedly, amylin produces substantial and brisk increases in both plasma glucose and lactate. As shown in Example 2 below, this hyperlactemia persisted for 1–2 hours and the hyperglycemia for 2–3 hours. These responses were associated with increased endogenous (hepatic) glucose production that persisted for 4–5 hours (compared to respective control groups). The significant increase of these responses over hypotensive controls indicate they result from a direct effect of amylin and not merely hypoperfusion. Similarly, the lack of measured differences in plasma catecholamines between treatment groups indicates that the observed effects were not caused by these agents. The observed excess of rates of glucose appearance over disposal leading to hyperglycemia with amylin occurred in spite of a prolonged fasting period. In such a fasting period, liver glycogen would typically be depleted to 0.2% (wt/wt) in rats. Shulman, G. I., et al., *J. Clin. Invest.* 76:1229–1236 (1985).

Figure 5:
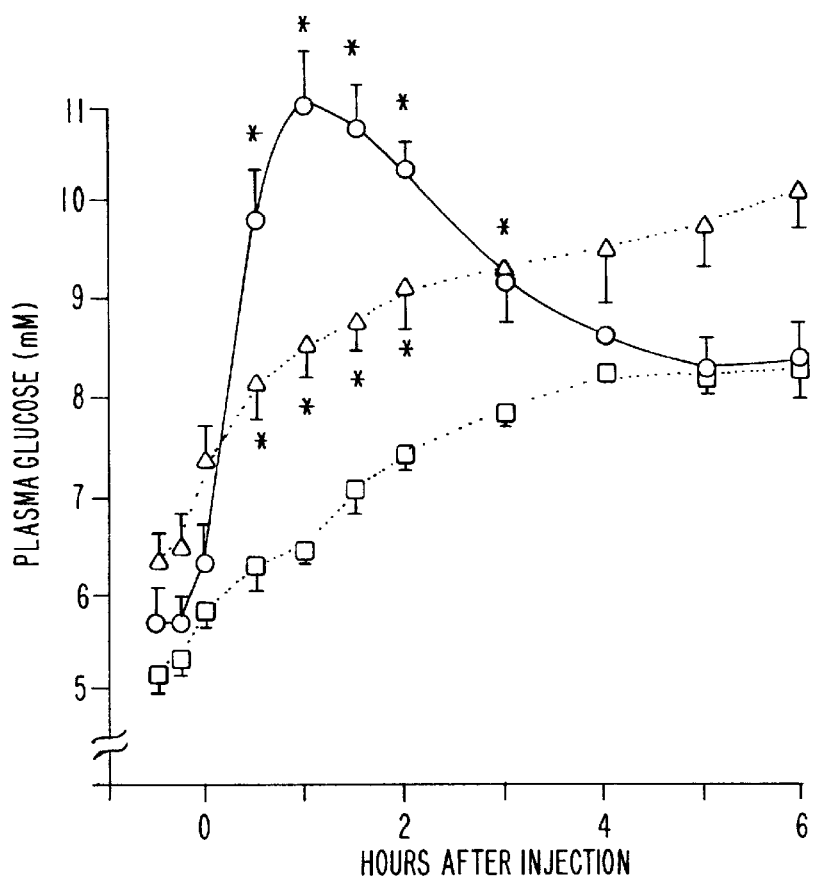
FIG. 5 shows the plasma glucose response (mean±SEM, n=6 for each curve) of rats infused with somatostatin (3.4 nmol/hr) and injected with 66 nmol/kg amylin (open circle), peptide control (open square), or phentolamine (open triangle) in a regimen that replicated the blood pressure response to amylin (BP control, open triangle). Asterisks above the symbols indicate differences between amylin-treated and peptide control groups. Asterisks below the symbols indicate differences between the amylin treated and BP control groups.
Figure 6:
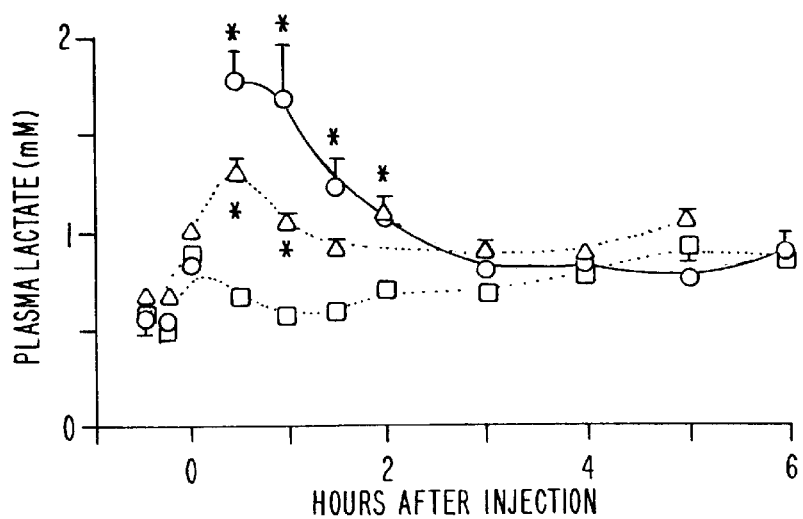
FIG. 6 shows the plasma lactate response (mean±SEM, n=6 for each curve) for groups described in FIG. 5. Symbols and asterisks have the same meaning as in FIG. 5.
Figure 7A:
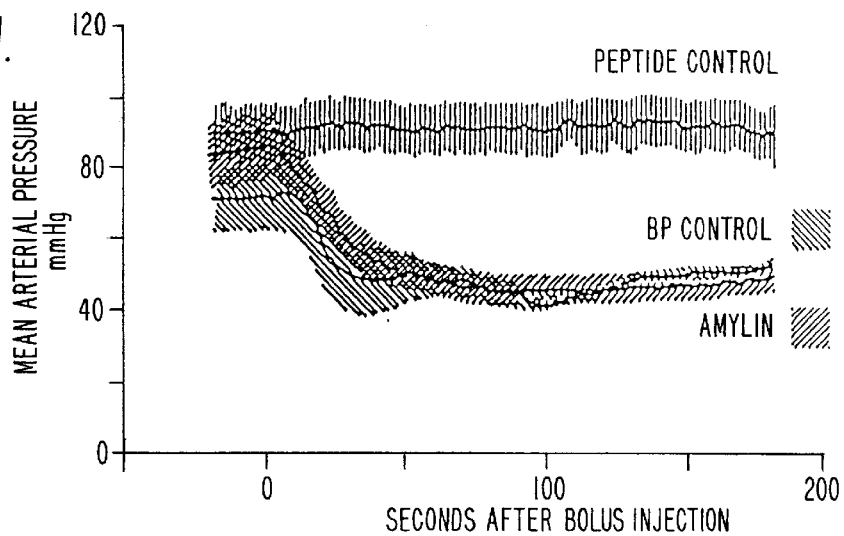
FIG. 7A shows the mean arterial blood pressure response (2-second means±S.E. indicated by shading) for rats injected with amylin (66 nmol/kg), peptide control or phentolamine in a schedule designed to replicate the amylin blood pressure response. Subacute blood pressure response is shown in FIG. 7B as mean arterial pressure (30-second means±S.E.). Symbols, error bars and asterisks have the same meaning as in FIG. 5. In addition, the acute blood-pressure response is plotted at the time of injection.
Figure 7B:
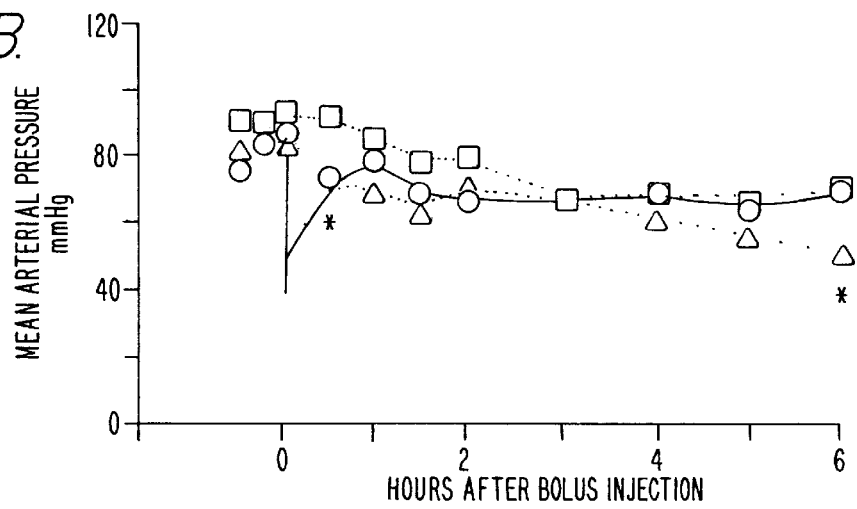
Figure 8:
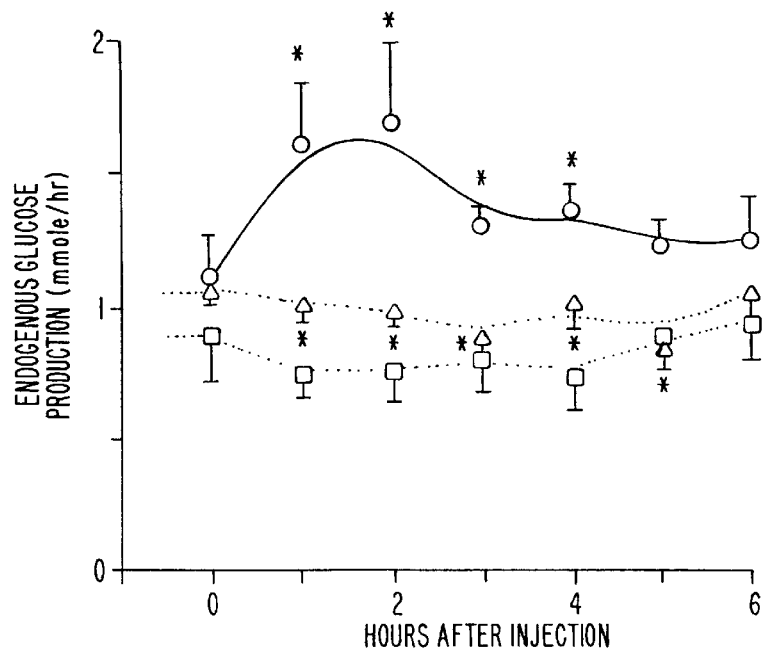
FIG. 8 shows isotopically determined, non-steady-state endogenous (hepatic) glucose production in rats injected intravenously with 25.5 nmol amylin (open circle), peptide control (open square) or phentolamine (open triangle) as described for the above FIGURES. Sample numbers and the meaning of symbols, bars and asterisks are the same as in FIGS. 5 and 6.

FIG. 5 shows that following injection of amylin, there was a rapid increase in plasma glucose. This rise was statistically greater than the slower, sustained rise in plasma glucose seen in control animals, and hyperglycemia remained for several hours. Plasma lactate results are shown in FIG. 6. Plasma lactate concentration increased by 230% within 30 minutes after injection of amylin and remained significantly elevated for at least two hours. Blood pressure results are shown in FIG. 7. Because there was a significant fall in mean arterial pressure under the experimental conditions, a blood pressure control group was designed to replicate these changes and allow assessment of the component of the hyperglycemia and hyperlactemia that might in any way be attributable to reduced tissue perfusion resulting from reduced arterial pressure. Over the six hour post-injection, however, there were no significant differences in arterial pressure between the amylin and phentolamine treated groups. On the other hand, there were significant differences in the glucose and lactate profiles between these two groups, indicating that such differences were not due to the vasoactive effects of amylin. As shown in FIG. 8, amylin also caused an increase of 214% in endogenous glucose production within one hour after injection. It remained elevated for four hours relative to controls.

The observed appearance of lactate in the plasma following amylin administration in FIG. 6 is consistent with its originating from muscle glycogenolysis, as described above. The hepatic glucose production and plasma glucose are significantly elevated over control values for longer than is the plasma lactate. While other studies have generally looked at amylin in regard to its ability to modulate insulin-mediated metabolic changes, somatostatin infusions were used as described below to inhibit endogenous insulin and glucagon secretion in determining the effects of amylin independent of changes in these hormones. A range of metabolic parameters following a single bolus dose of amylin was observed. The sequence of observed effects is consistent with the determination that, following an amylin bolus, muscle lactate is released into the plasma and supplied to the liver where it serves as a substrate for gluconeogenesis. That is, amylin enhances Cori cycling. It controls flux through the Cori (glucose to 3-carbon compound to glucose) cycle by modulating gluconeogenic substrate release from peripheral tissues and gluconeogenesis/glycogenolysis in the liver. Post-prandial flux through the Cori cycle appears to be a major mechanism of liver glycogen repletion. Newgard, C. B., Hirsch, L. J., Foster, D. W. & McGarry, J. D., *J. Biol. Chem.* 258:8046–8052 (1983).

Example 3 investigated the effects of amylin and glucagon bolus injections on plasma glucose and lactate levels in fasted rats. As shown in the FIGS. 9A and 9B, amylin caused a rapid rise in both plasma glucose and lactate under unclamped conditions (the experiments described in Example 2 having been done under somatostatin clamp). The rise in glucose was significant by 30 minutes and peaked at 1.5±0.22 hours. The increase in lactate levels peaked within 30 minutes after injection, however. In contrast, injection of glucagon caused a glycemic response that was significant, but much less than that caused by amylin. Glucagon did not, however, induce a significant change in lactate relative to controls.

In the studies described in Example 4, the effect of glucagon administration (at 0 hours) followed by a subsequent administration of amylin (6 hours) was observed in both fasted (20±1 hours) and fed rats. See FIG. 10 and Table 1. In fed rats, glucagon injection produced a rapid glycemic response that persisted for about 0.6 hrs. Glucagon is thought to exert its immediate effects through direct stimulation of hepatic glycogenolysis, which in man initially accounts for 85% of counter-regulatory hepatic glucose production. It has been reported that prolonged counter-regulatory hormone stimulation results in gluconeogenesis gradually replacing glycogenolysis as the mode of hepatic glycogenesis (Lecavalier, L., et al., *Am. J. Physiol.* 256:844–51 (1989)).

In contrast, there was a lesser glycemic response to glucagon in 20-hour fasted rats. In fasted rats, hepatic glycogen is minimal at 18–24 hours, being about 0.1–0.2% wt/wt. Although hepatic glycogen content was not measured in this study, the data observed were consistent with hepatic glycogen depletion limiting glycogenesis following glucagon injection.

In fasted animals, amylin injection resulted in an abrupt increment in plasma lactate and a profound increase in plasma glucose that mirrored a relatively rapid decay in lactate. In fed animals there was an increase in plasma lactate approximately equal to that observed in fasted animals. However, compared to the fasted animals, there was a diminished glycemic response that was matched by a slower decay in plasma lactate.

Figure 12A:
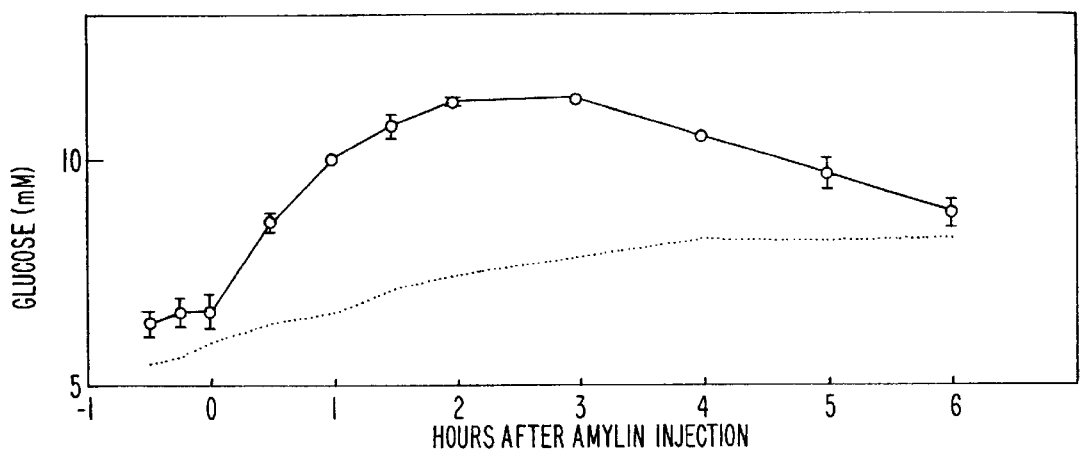
FIG. 12A, 12B and 12C. Glycemica/lactemic/blood pressure responses to s.c. amylin. Plasma glucose (upper panel), plasma lactate (middle panel) and mean arterial pressure (lower panel) following subcutaneous injection of 25.5 nmol rat amylin (__), n=2. The control response from FIG. 11 is overlaid for comparison (...). Symbols represent the mean±SEM.
Figure 12B:
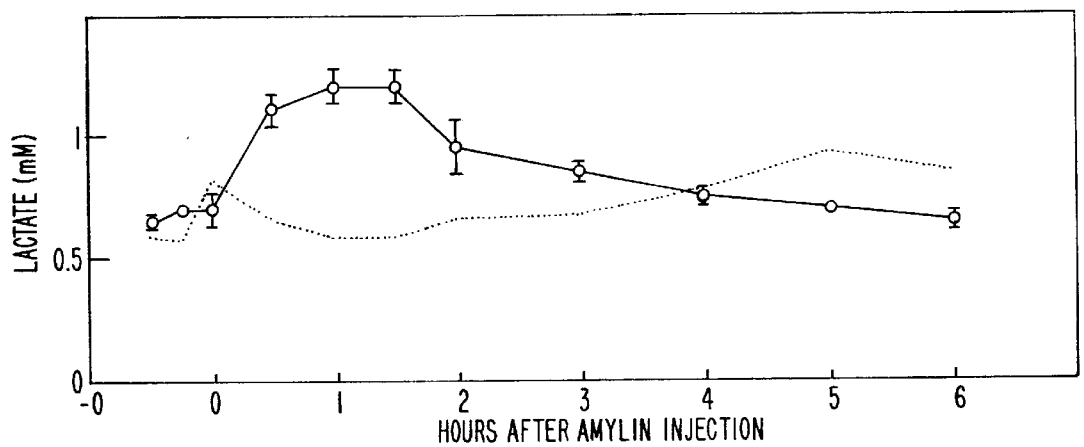
Figure 12C:
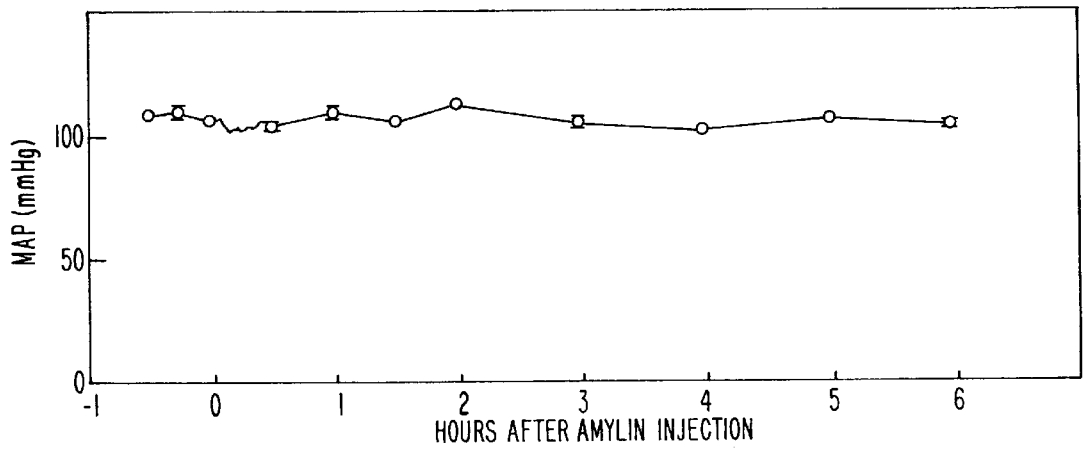
Figure 13A:
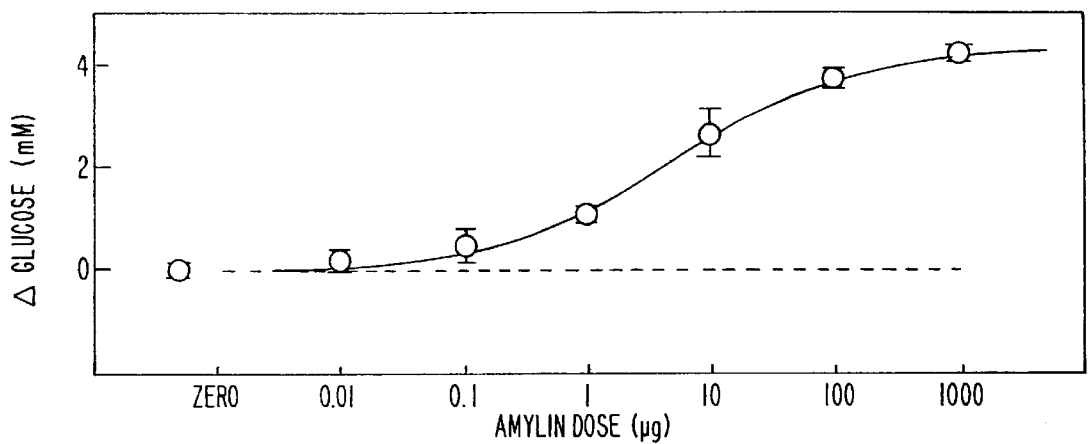
FIGS. 13A, 13B and 13C. Amylin dose responses for changes in glucose, lactate and arterial pressure. The increment in plasma glucose (upper panel) and lactate (middle panel) measured at 30 minutes post-injection subtracts the response to saline injection (0.45 mM, −0.07 mM respectively). The mean arterial pressure response (lower panel) is the change 1 minute post-injection.
Figure 13B:
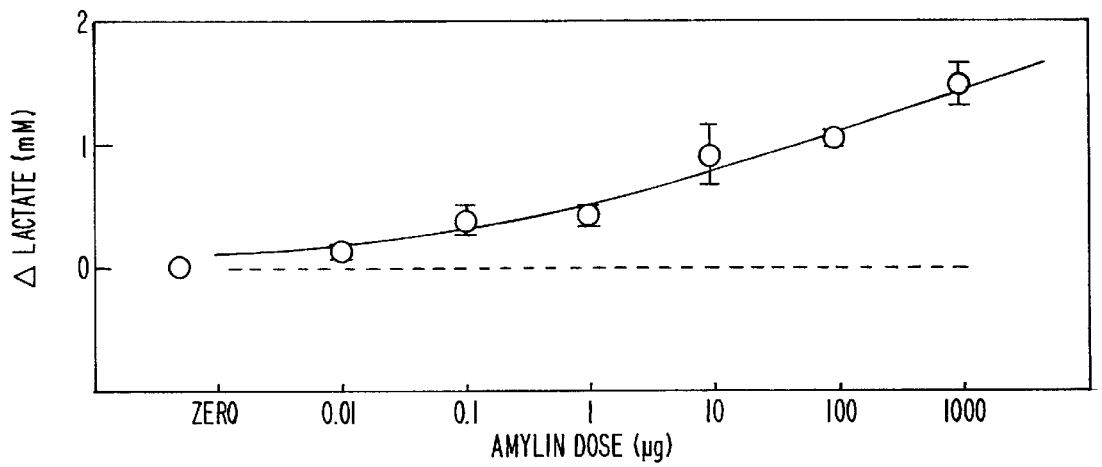
Figure 13C:
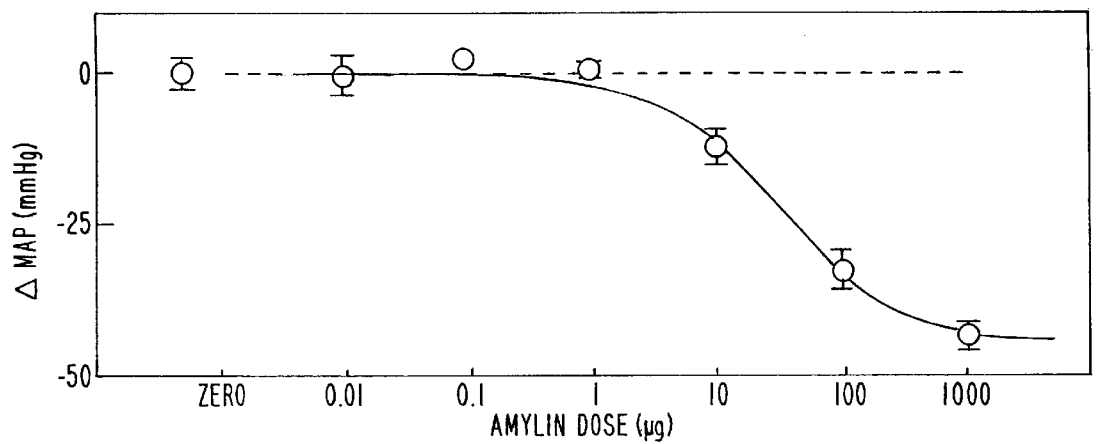

Example 6 below shows that amylin evokes dose-dependent increases in plasma lactate and glucose in lightly anaesthetized rats. See FIGS. 11–13. The results also indicate these metabolic responses are not a consequence of the cardiovascular changes which larger doses of amylin can elicit. First, the subcutaneous injection of 100 µg amylin causes no significant change in blood pressure, in contrast to the transient drop evoked by an intravenous bolus of the same dose; yet the plasma lactate and plasma glucose were substantially increased, the glucose from 6.5 mM to 12 mM and the lactate from 0.15 to 1.25 nM. See FIG. 12. The rise time of the responses was somewhat slower and the decline extended following sub-cutaneous injection, in line with the slower access of amylin to the blood stream with this route of administration. The areas under the glucose and lactate response curve (integral of experimental minus control curves) were not significantly different for the intravenous and subcutaneous routes of administration. Second, the dose response measurements in FIG. 13 show that the dose response curve for glucose and lactate appears to be left shifted compared to the blood pressure response; thus there are intravenous doses of amylin which elicit a metabolic response but no detected cardiovascular response. These experiments which monitor simultaneously metabolic and cardiovascular effects of amylin and show the former in the absence of the latter are novel. It will be appreciated that changes in blood flow and perfusion pressure can increase lactate production by muscle due to ischemic hypoxia and increases in hepatic glucose output by activation of the sympathoadrenal system and elevation of catecholamine levels. The experiments shown in Examples 2 and 6, also support the determination that amylin actions are not substantially mediated via increased glucagon secretion.

An important feature of these results is that the increase in plasma lactate appears as the most pronounced amylin action so far studied, in that it is seen at the lowest doses, is similar in size in the fed and fasted states and appears to precede the hyperglycemic response. The amylin-evoked hyperlactemia is consistent with a primary effect of amylin on skeletal muscle which is clearly directly responsive to amylin in vitro. We believe that the mechanism undergirding this action is stimulation of glycogenolysis, as described above and in the Example 1 experimentals related to the amylin-mediated stimulation of phosphorylase a in isolated soleus muscle. It is important to note that the actions of amylin in increasing plasma lactate, and activating phosphorylase are independent of insulin action; the hyperlactemic response was seen in somatostatin-treated animals and the phosphorylase activation occurred in muscle incubated in insulin-free medium.

Figure 14:
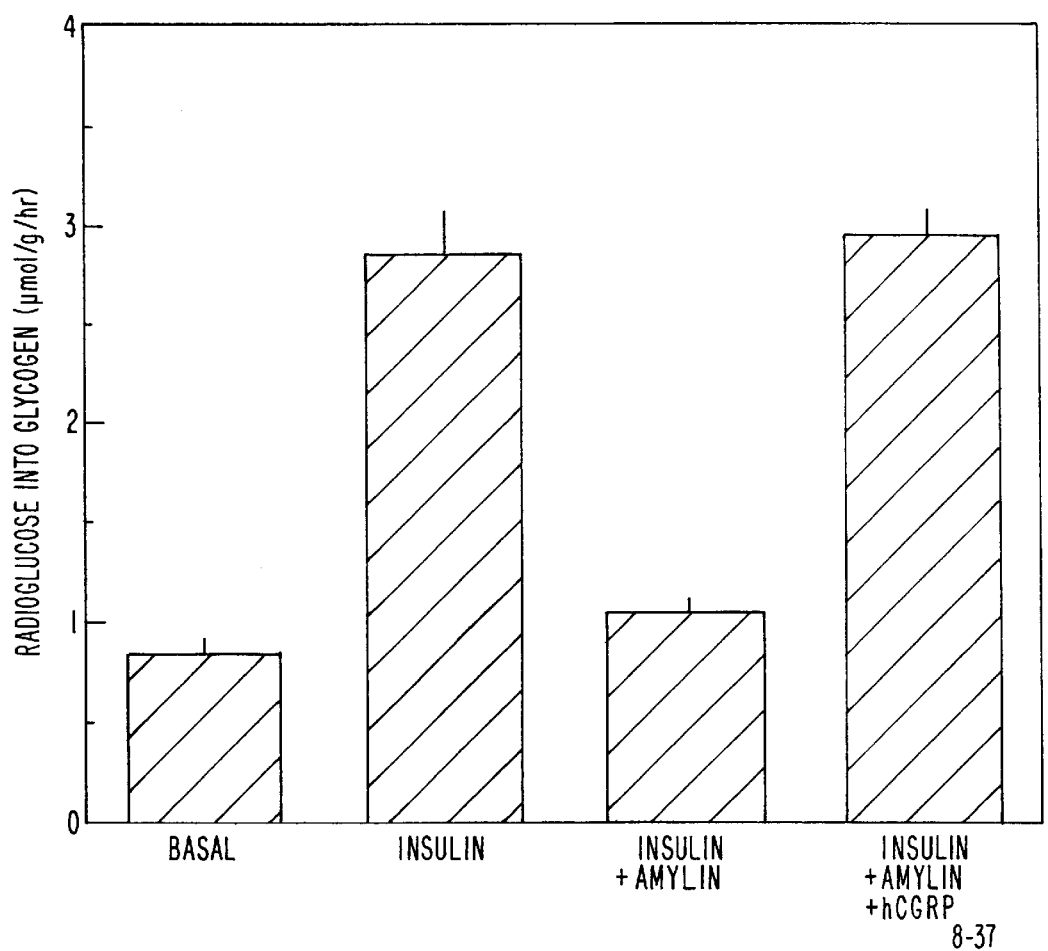
FIG. 14. In vitro agonist and antagonist activity. Isolated soleus muscles were pre-incubated for 30 minutes in Krebs-ringer bicarbonate buffer containing no added hormones (Control), 7.1 nM insulin, 7.1 nM insulin +100 nM amylin, and 7.1 nM insulin +100 nM amylin +100 μM hCGRP$_{8-37}$. Net incorporation of U-$^{14}$C-glucose added to the medium for the next hour was measured in extracted glycogen. n=12 muscle strips, means±s.e.m.
Figure 15:
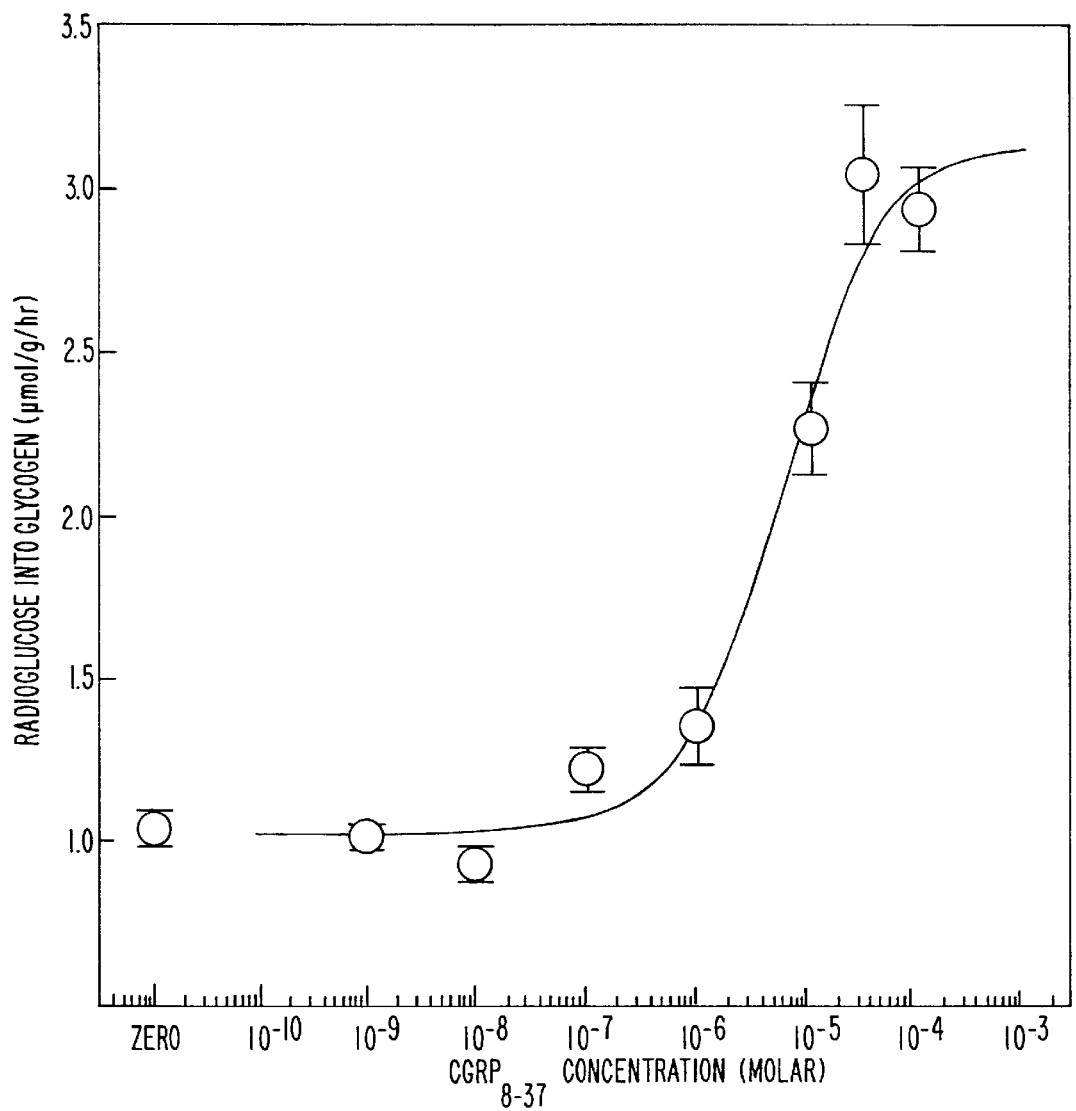
FIG. 15. In vitro dose response. In vitro dose-response for the antagonism of the effect of 100 nM amylin to inhibit U-$^{14}$C-glucose incorporation in glycogen in soleus muscle. The EC$_{50}$ was 5.92 μM±0.13 log units.
Figure 16:
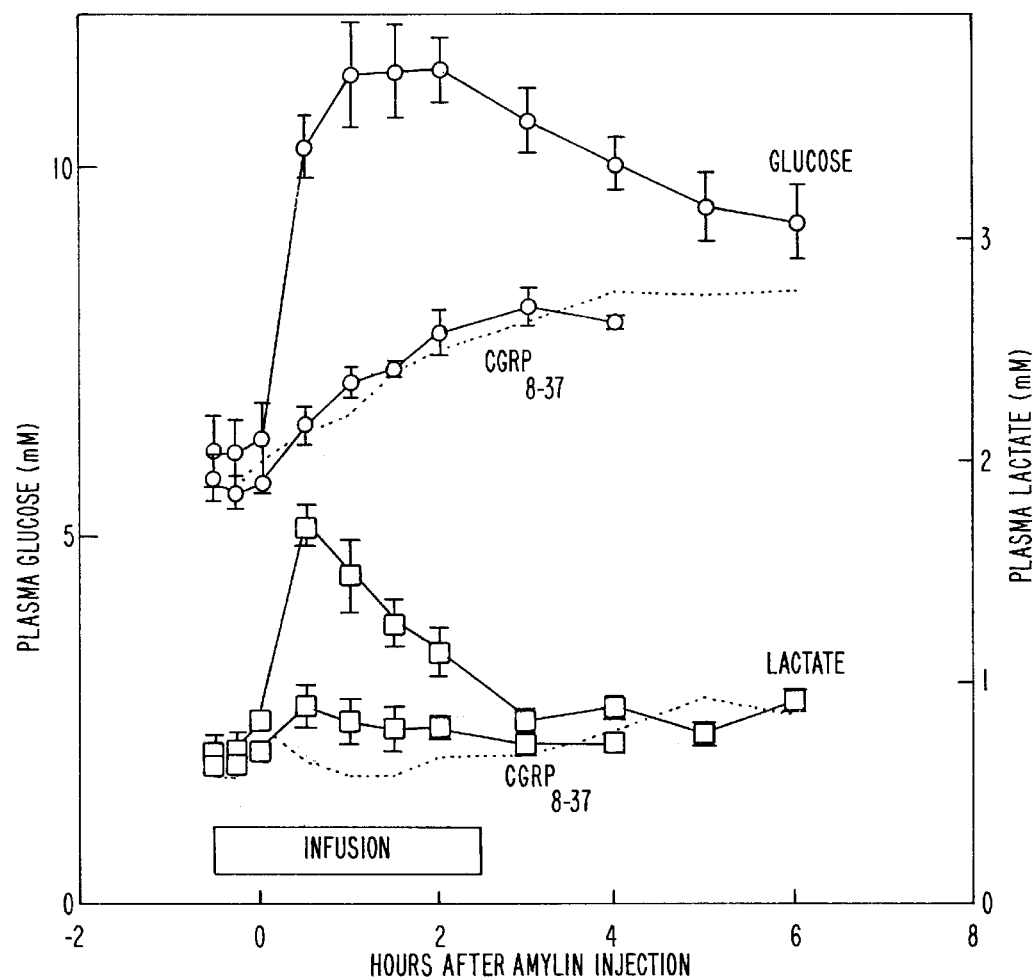
FIG. 16. In vivo amylin agonist and antagonist responses. Amylin-induced changes in plasma lactate (_) and glucose (O) without (n=7) and with (n=3) a primed-continuous hCGRP$_{8-37}$ preinfusion (lower traces). The response to saline alone (...; n=7) is also shown. Symbols represent the means±s.e.m.

The experiments in Example 7 describe the effects of human $CGRP_{8-37}$ as an amylin antagonist in vitro and in vivo. Its effects on amylin-induced changes in blood pressure were also investigated. In vitro results are shown in FIGS. 14 and 15, where insulin is seen to stimulate the incorporation of radio-labelled glucose into glycogen in the soleus muscle assay. The addition of amylin to the test system causes an inhibition of the effect of insulin. When human $CGRP_{8-37}$ is added to the test system, the amylin inhibition of insulin is reversed. This antagonist had no effect when administered alone. FIG. 15 shows the dose-dependent effects of the antagonist human $CGRP_{8-37}$. In vivo results are shown in FIG. 16, where human $CGRP_{8-37}$ completely antagonized the effect of amylin to elevate blood levels of lactate and glucose.

The following Examples are illustrative, and supportive of the assay methods described and claims herein, but not limiting of the methods of the present invention.

EXAMPLE 1

These experiments demonstrate the ability of amylin to enhance glycogen breakdown by the indirect stimulation of glycogen phosphorylase a. Harlan Sprague Dawley rats (200 g males) were housed at 22.7±0.8° C. in a 12:12 hour light:dark cycle (experiments being performed during the light cycle) and fed and watered ad libitum (Diet LM-485, Teklad, Madison, Wis.). Animals were fasted for 4 hours before experimentation.

The activity of the rat amylin used in this study (lot #ZG485, Bachem, Torrance, Calif.) was first determined using the soleus muscle-based assay. The measured $EC_{50}$ was 6.7±1.5 nM. Concentrations of amylin in protein-free buffers were determined by quantitative amino acid analysis as previously described. Cooper G. J. S. et al., *Proc. Nat. Acad. Sci. USA*, 85:7763–7766 (1988). Soluble insulin, Humulin-R 100 U/ml, was purchased from Eli Lilly & Co., Indianapolis, Ind. The conversion factor between activity units, U, and molar units for insulin used in the present study was 1 µU/ml=7.1 pM. All other reagents were of analytical grade or better unless otherwise stated.

Isolation and incubation of isolated, stripped rat soleus muscles in the presence of various concentrations of insulin and amylin were performed according to previously described methods. Leighton, B. and Cooper, G. J. S., *Nature* 335:632–635 (1988); Leighton et al., *FEBS Lett.* 249:357–361 (1989). Four muscle strips were incubated at each treatment condition.

Control incubations were performed in the absence or presence of insulin (7.1 nM) or amylin (34 nM). Dose dependent effects of amylin on glycogen phosphorylase a activity were studied in the presence of constant insulin (7.1 nM), at increasing concentrations of amylin (0, 0.39, 3.9, 76, 781 nM).

After incubation, muscles were snap frozen in liquid nitrogen, then stored at −70° C. until measurements of glycogen phosphorylase a activity were made.

Activity of glycogen phosphorylase a in extracts of powdered, frozen muscle was determined using a previously described method. Tan, A. W. and Nuttall, F. Q., *Biochim. Biophys. Acta* 410:45–60 (1975). Enzyme activity is expressed as nmol.glucosyl units transferred/min/ mg.protein. Concentrations of protein in muscle tissue extracts were measured according to the method of Bradford. Bradford, M. M., *Analyt. Biochem.* 72:248–254 (1976).

All results are presented as mean±SEM. Statistical analysis was performed using the non-paired, two-tailed Student's t-test, with significance levels as stated.

Treatment of isolated rat skeletal muscle with 34 nM amylin in the absence of insulin increased the activity of muscle glycogen phosphorylase a by 2.8-fold, from a basal level of 8.5±0.8 nmol/min/mg.protein to 23.7±4.1 nmol/min/mg.protein ($P<0.0001$). See FIG. 3.

EXAMPLE 2

Each treatment of the experimental design used 6 male Harlan Sprague Dawley rats (body mass 388±7 g, age 93±2 days). Animals were housed at 22.7±0.8° C. in a 12:12 hour light:dark cycle (experiments being performed during the light cycle) and fed and watered ad libitum (Diet LM-485, Teklad, Madison, Wis.). Animals were overnight fasted (13.3±2.8 hours before surgery). Anesthesia was induced with 5% halothane, maintained at 2% during surgery and at 0.8–1% during metabolic recordings. Tracheotomy and cannulation of right femoral artery and vein were performed.

The femoral arterial line was connected to a pressure transducer (Spectramed P23XL transducer, Model 13-4615-58 amplifier, Gould, Cleveland, Ohio) and perfused with heparinized saline (2 U/ml) at 3.0 ml/hr. All chronically infused agents were added to this infusate. The femoral venous line was used for acute (bolus) injections.

A 4-limb ECG was monitored via an ECG/biotach amplifier (Model 13-4615-65A, Gould, Cleveland, Ohio) and heart rate derived.

Colonic temperature was measured using a thermistor probe and controller (Model 73A, YSI, Yellow Springs, Ohio) which provided closed-loop control of core temperature by switching a heated operating table.

The endotracheal tube was connected to a specially constructed pneumotach which measured the pressure differential across a small constriction in the tracheal flow. The output was linearized on-line to flow using a calibration table (Labtech Notebook function). A sample of the tracheal flow was continuously analyzed for $N_2$, $O_2$, Ar, $CO_2$, water vapor and halothane using a respiratory mass spectrometer (MGA 3000, Airspec, Biggin Hill, Kent, England).

Signals for tracheal flow, $O_2$ and $CO_2$ concentration, heart rate, arterial pressure and colonic temperature were periodically sampled and stored with 12-bit precision at 20 Hz using a computerized data acquisition system (DT2801A A/D converters, DataTranslation, Marlboro, Mass.; AST Premium 386 computer, AST Research, Irvine, Calif.; Labtech Notebook software, Laboratory Technologies Corp, Wilmington, Mass.). Gas tension and flow signals were synchronized and used to derive oxygen consumption rates and respiratory quotient over 30-second epochs. Upon cannulation, animals were infused with heparinized saline containing somatostatin (S-9129, Sigma, St Louis, Mo.), 3.4 nmol/hr and 3-[$^3$H]-glucose (New England Nuclear/DuPont, Wilmington, Del.), 44.4 kBq/hr.

Upon cannulation, animals were infused with heparinized saline containing somatostatin (S-9129, Sigma, St. Louis, Mo.), 3.4 nmol/hour and 3-[$^3$H]-glucose (New England Nuclear/DuPont, Wilmington, Del.).

There were three treatment groups:

(1) Amylin Bolus (n=6): After 2-hours infusion, animals were injected with a 100 ml bolus of saline containing 25.5 nmol freshly dissolved rat amylin (lot#ZG485, Bachem, Torrance, Calif.). Bioactivity of peptide to be used in this study was first verified using a soleus muscle-based assay (Leighton, B. and Cooper, G. J. S., *Nature* 335:632–635 (1988) ($EC_{50}$=6.7±1.5 nM).

(2) Controls (n=6): Instead of fresh amylin, rats were injected with either 25.5 nmol of the same peptide autoclaved at 121° C. for 90 minutes (n=3) or saline alone (n=3). Since there were no differences between responses to either autoclaved amylinor saline, data have been pooled into a single control group referred to as "peptide controls".

(3) Blood Pressure Controls (n=6): Instead of fresh amylin, 18 nmol pulses of phentolamine in 50 $\mu$l of saline were injected via the femoral venous cannula in a schedule calculated to mimic the transient hypotensive profile produced by the 66 nmol/kg amylin bolus.

Arterial samples were drawn 0.5, 0.25 and 0 hr before bolus injection, and 0.5, 1, 1.5, 2, 3, 4, 5 and 6 hr after injection. Samples were collected into $Na_2$. EDTA (final concentration approximately 5 mM), and separated plasma analyzed for glucose, lactate, tritiated glucose, insulin and rat amylin.

Glucose and lactate were analyzed by immobilized enzyme chemistries (glucose oxidase, L-lactate oxidase, Analyzer model 2300-STAT, YSI, Yellow Springs, Ohio).

Tritiated glucose specific activity was determined after counting the tritium remaining after evaporation of plasma previously stripped of protein by perchloric acid precipitation. Best, J. D., Judzewitsch, Pfeiffer, M. A., Beard, J. C., Halter, J. B. & Porte, D., *Diabetes* 31:333–338 (1982). With steady infusion rates of radioglucose (44.4 kBq/hr), rates of endogenous glucose production were determined from tritiated glucose specific activity and an assumed glucose space using a modification (Proietto, J., Rohner-Jeanrenaud, F., Ionescu, E., Terretaz, J., Sauter, J. F. & Jeanrenaud, B., *Am. J. Physiol.* 252:E77–E84 (1987)) of Steele's non-steady-state tracer dilution method. Steele, R., *Ann. NY Acad. Sci.*, 8:420–430 (1959).

Insulin was determined by radioimmunoassay (Micromedic human insulin RIA kit, ICN Biomedicals, Horsham, Pa.), sensitivity 6 pM, cross-reactivity to rat insulin 89.5%. Rat amylin was determined by radioimmunoassay (Kit RIK7323, Peninsula Laboratories, Belmont, Calif.) following C-18 resin extraction and elution with 80% acetonitrile/0.1% trifluoroacetic acid.

Plasma catecholamines (epinephrine and norepinephrine) were measured at 0, 2, 4 and 6 hours post-injection using HPLC with electrochemical detection following plasma extraction with alumina. A modification of the method of Weicker et al. (Weicker, H., Feraudi, M., Hagle, H. & Pluto, R., *Clin. Chim. Acta* 141:17–25 (1984)), whereby internal standard (dihydroxybutyric acid) was added to plasma prior to extraction enabled analysis of 50 $\mu$L samples with a coefficient of variation of 7.8%.

Statistical analyses were by Student's t-test routines contained in the SYSTAT system (Systat, Evanston, Ill.) using $p<0.05$ as the level of significance. Unless stated otherwise, all results are reported as means +standard error of the mean.

Measured blood glucose and lactate levels are shown in FIG. 5. Following injection of amylin (66 nmol/kg) there was a rapid increase in plasma glucose from 5.9±0.3 mM to 11.0±0.6 mM glucose. In contrast, prolonged experimental conditions produced a slower, sustained rise in plasma glucose in control animals. Amylin treated rats (group 1) remained significantly hyperglycemic relative to inactive-peptide controls (group 2) for at least 3 hours, and relative to the blood pressure controls for at least 2 hours. FIG. 6 shows that plasma lactate concentration had increased 230% by 30 minutes after injection and remained significantly elevated for at least 2 hours.

There was a significant fall in mean arterial pressure following 2 hours somatostatin infusion from 101±2 to 83±5 mmHg, (13.47±0.27±11.07 0.67 kPa, P<0.01). In addition, with the bolus amylin injection, there was a further fall in mean arterial pressure that was complete within about 60 seconds. Blood pressure was still significantly lower (73 versus 91 mmHg) and heart rate significantly higher (336 versus 320 beats/min) in the amylin injected group 30 minutes post injection but both had returned to peptide control levels (group 2) by 60 minutes post-injection (see FIG. 7B).

The blood pressure control group (group 3) was designed to replicate the change in arterial pressure produced by the vasoactivity of this large dose of amylin in the presence of a somatostatin infusion, and thereby gauge the component of the hyperglycemia and hyperlactemia that might be attributable to reduced tissue perfusion resulting from reduced arterial pressure.

Over the 6 hour post-injection period, there were no significant differences in mean arterial pressure between amylin- and phentolamine-treated groups. FIG. 7A illustrates the arterial pressure response to repetitive pulses of 18 nmol of phentolamine in comparison to the target (group 1) pressure profile. In this group there was an increased glucose and lactate response over the normotensive controls. However, it was not as great and had a clearly different temporal profile to the amylin response shown in FIGS. 5 and 6.

Blood catecholamine (norepinephrine) levels did not differ in any of the treatment group comparisons (amylin treated versus peptide controls; amylin treated versus blood pressure controls; peptide controls versus blood pressure controls) at any of the 4 time points (0, 2, 4, 6 hours post-injection), except on one occasion (peptide control value>amylin treated group at 2 hours). In neither a pooled data set from all 3 treatment groups nor from just the hypotensive groups (amylin treated+blood pressure controls), was there a significant increment in norepinephrine over pre-injection levels. Epinephrine levels, analyzed in the same way showed no significant differences at any time point for any comparison, and no increment with time in pooled data sets. Plasma norepinephrine levels were 3.9±0.4, 5.1±0.6, and 3.9±0.3 nM, and plasma epinephrine levels were 4.1±0.9, 3.7±0.4, and 5.5±0.8 nM in amylin-treated, peptide control and blood pressure control groups respectively.

With regard to blood insulin levels there was no change in plasma insulin concentration from the pre-injection level in any of the treatment groups over the duration of the experiment, indicating that somatostatin had effectively inhibited any hyperinsulinemia that may have been expected from the observed hyperglycemic episodes. Similarly, there was no difference between treatment groups at any of the time points throughout the experiment (0, 2, 4, 6 hours). Glucose-stimulated insulin secretion was effectively inhibited by somatostatin infusion to ensure that glucagon secretion was inhibited as well. Gerich, J. E., Lorenzi, M., Schneider, V., Kwan, C. W., Karam, J. H., Guillemin, R. & Forsham, P. H., *Diabetes* 23:876–880 (1974). Plasma insulin levels were 128±21, 184±22, and 153±15 pM in the amylin-treated, peptide control and blood pressure control groups respectively.

Isotopically determined endogenous glucose production in the amylin injected group increased to 214% and 219% of the corresponding control values at 1 and 2 hours post-injection respectively, and remained significantly elevated (compared to both the peptide controls and to the pre-injection level) for 4 hours. See FIG. 8. Amylin injection resulted in an initial rate of increase in plasma glucose concentration of 0.12 mM/min. When distributed throughout the estimated glucose space (97 ml), this converts to an excess of glucose appearance over glucose disappearance of 11.3 $\mu$mol/min. This increase represents an approximate doubling of the resting rate of glucose production over that measured in controls (13.5 $\mu$mol/min).

Similarly, endogenous glucose production in the amylin injected group remained significantly elevated compared to the blood pressure controls for 5 hours post injection. As shown in FIG. 8, the control groups did not differ from each other at any time point.

Rates of oxygen consumption did not change over the course of the experiment in either the experimental or peptide control group. Nor were they different between groups (7.89±0.38 and 7.44±0.34 ml/min respectively pre-injection, versus 7.82±0.55 and 7.32±0.26 ml/min at the time of peak glycemic response [1 hour post-injection]).

Respiratory quotients (RQ) after overnight fasting were near the theoretical minimum after overnight fasting in amylin treated animals (0.720±0.014) and peptide controls (0.747±0.018). There were no changes in RQ from pre-injection values following amylin injection, and no differences between amylin treated and peptide control groups.

EXAMPLE 3

In this Example the effects of amylin and glucagon on plasma glucose and lactate in fasted, anesthetized rats were compared.

Sixteen male Harlan Sprague Dawley rats were housed at 22.7±0.8° C. in a 12:12 hour light:dark cycle (experiments being performed during the light cycle) and fed and watered ad libitum (Diet LM-485, Teklad, Madison, Wis.). Animals were overnight fasted prior to experimentation. Anesthesia was induced with 5% halothane, maintained at 2% during surgery and at 0.8–1% during metabolic recordings. Tracheotomy and cannulation of right femoral artery and vein were performed.

The femoral arterial line was connected to a pressure transducer (Spectramed P23XL transducer, Model 13-4615-58 amplifier, Gould, Cleveland, Ohio) and perfused with heparinized saline (2 U/ml) at 3.0 ml/hr. All chronically infused agents were added to this infusate. The femoral venous line was used for acute (bolus) injections. A 4-limb ECG was monitored via an ECG/biotach amplifier (Model 13-4615-65A, Gould, Cleveland, Ohio) and heart rate derived.

Colonic temperature was measured using a thermistor probe and controller (Model 73A, YSI, Yellow Springs, Ohio) which provided closed-loop control of core temperature by switching a heated operating table. Signals for heart rate, arterial pressure and colonic temperature were periodically sampled and stored with 12-bit precision at 20 Hz using a computerized data acquisition system (DT2801A A/D converters, DataTranslation, Marlboro, Mass.; AST Premium 386 computer, AST Research, Irvine, Calif.;

Labtech Notebook software, Laboratory Technologies Corp, Wilmington, Mass.).

There were three treatment groups:
1. Amylin Bolus (n=6; mass=310±7 g; age=110±2 d; fasted 20.0±0.7 hr). After 2-hours infusion, animals were injected with a 100 μl bolus of saline containing 25.5 nmol freshly dissolved rat amylin (lot#ZG485, Bachem, Torrance, Calif.). Bioactivity of peptide to be used in this study was first verified using the soleus muscle-based assay ($EC_{50}$=6.7±1.5 nM).
2. Glucagon Bolus (n=6; mass=331±5 g; age=76±1 d; fasted 18.7±0.4 hr; structures of rat and human glucagon are identical). After 2-hours infusion and taking of basal samples, animals were injected with 28.7 nmol glucagon in a 100 μl bolus of diluent (Glucagon for injection USP, Eli Lilly and Company, Indianapolis, Ind.; lot#4MC51D, contains glucagon 1 mg, lactose 49 mg constituted into 1 ml aqueous solution of 1.6% glycerin and 0.2% phenol). Following 6 hours observation of the glucagon response, 25.5 nmol of rat amylin (as per group 1) was injected and the response followed for a further 2 hours.
3. Controls (n=3; mass=354±17 g; age=82±1 d; fasted 19.5±0.7 hr). Control animals were injected with saline alone.

Arterial samples were drawn 0.5, 0.25 and 0 hr before bolus injection, and 0.5, 1, 1.5, 2, 3, 4, 5, 6 hr after injection (group 1), and at 6.5, 7, 7.5 and 8 hours (group 2). Arterial samples were collected into heparinized capillaries and separated plasma analyzed immediately for glucose and lactate using immobilized enzyme chemistries (glucose oxidase, L-lactate oxidase, Analyzer model 2300-STAT, YSI, Yellow Springs, Ohio). Statistical analyses were by Student's t-test routines contained in the SYSTAT system (Systat, Evanston, Ill.). Unless stated otherwise, all results are reported as means ± standard error of the mean.

Results are plotted in FIG. 9A and 9B. Amylin injection (i.v. bolus of 25.5 nmol) resulted in a rapid increase in both plasma glucose and lactate. Elevations of plasma glucose above control were significant at 30 minutes and persisted beyond 2 hours. The peak glycemic response occurred at 1.50±0.22 hours and represented a 5.59±0.46 mM increment above preinjection levels. Plasma lactate levels peaked within 30 minutes of injection, with a 136% increment of 1.02±0.11 mM over preinjection levels of 0.75±0.06 mM (increment vs control, $p<0.001$).

Glucagon injections (i.v. bolus of 28.7 nmol) resulted in a peak glycemic response of 1.94±0.34 mM which occurred 1.58±0.24 hours after i.v. injection (see FIG. 9A). The glycemic response to glucagon was less than to either of the amylin responses (35% of the amylin-alone response, $p<0.001$; 35% of the amylin-after-glucagon response, $p<0.003$). Compared to control animals, there was negligible increment in plasma lactate with glucagon (0.09±0.04 mM) (see FIG. 9B).

Six hours after glucagon injection, amylin (i.v. bolus of 25.5 nmol) resulted in a glycemic response of 5.60±0.86 mM, peaking 1.67±0.17 hours post-injection, and a brisk lactate response of 3.44±0.42 mM, peaking within 30 min of injection (see FIG. 9A and 9B). The magnitude of the amylin-induced lactate response following glucagon was 3.4 times greater than that with amylin alone ($p<0.001$). The magnitudes of the glycemic responses were almost identical ($p=0.99$).

The t½ for the decline of amylin-generated glucose were 175 and 59 minutes for amylin alone and amylin after glucagon respectively. The corresponding values for lactate were 55 and 34 minutes. There were no significant differences in mean arterial pressure comparing amylin alone versus control, amylin alone versus glucagon or amylin alone versus amylin after glucagon for any of the comparable time points before and after injection.

EXAMPLE 4

In this Example the effects of glucagon administration (0 hours) followed by amylin administration (6 hours) on plasma glucose and lactate in fed and fasted (20±1 hours) rats was compared.

Male Harlan Sprague Dawley rats were housed at 22.7±0.8° C. in a 12:12 hour light:dark cycle (experiments being performed during the light cycle) and fed and watered ad libitum (Diet LM-485, Teklad, Madison, Wis.). Fasted animals were deprived of food 20±1 hours prior to experimentation. Fed animals were allowed access to food until surgery. Anesthesia was induced with 5% halothane, maintained at 2% during surgery and at 0.8–1% during metabolic recordings. Tracheotomy and cannulation of the right femoral artery and saphenous vein were performed.

The femoral arterial line was connected to a pressure transducer (Spectramed P23XL transducer, Model 13-4615-58 amplifier, Gould, Cleveland, Ohio) and perfused with heparinized saline (2 U/ml) at 3.0 ml/hr. All chronically infused agents were added to this infusate. The venous line was used for acute (bolus) injections.

A 4-limb ECG was monitored via an ECG/biotach amplifier (Model 13-4615-65A, Gould, Cleveland, Ohio) and heart rate derived.

Colonic temperature was measured using a thermistory probe and controller (Model 73A, YSI, Yellow Springs, Ohio) which provided closed-loop control of core temperature by switching a heated operating table.

Signals for heart rate, arterial pressure and colonic temperature were periodically sampled and stored with 12-bit precision at 20 Hz using a computerized data acquisition system (DT2801A A/D converters, DataTranslation, Marlboro, Mass.; AST Premium 386 computer, AST Research, Irvine, Calif.; Labtech Notebook software, Laboratory Technologies Corp., Wilmington, Mass.).

There were two treatment groups.
1. Glucagon Bolus+Amylin Bolus, Fasted (n=6; mass-331±5 g; age=76±1 day; fasted 18.7+0.4 hours). Structures of rat and human glucagon are identical. After 2-hours infusion and taking of basal samples, animals were injected with 86.4 nmol/kg glucagon in a 100 μl bolus of diluent (Glucagon for injection USP, Eli Lilly and Company, Indianapolis, Ind.; lot#4MC51D, contains glucagon 1 mg, lactose 49 mg constituted into 1 ml aqueous solution of 1.6% glycerin and 0.2% phenol). Following 6 hours observation of the glucagon response, 76.8 nmol/kg of rat amylin (as per group 1) was injected and the response followed for a further 4 hours.
2. Glucagon Bolus+Amylin Bolus, Fed (n=9; mass=322±11 g; age=63±3 day; fasted 0 hour). Other than having continued access to food, these animals were treated identically to those in group A.

Arterial samples were drawn 0.5, 0.25 and 0 hour before bolus injection, and 0.5, 1, 1.5, 2, 3, 4, 5, 6, 6.5, 7, 7.5, 8, 9 and 10 hours after injection. Arterial samples were collected into heparinized capillaries and the separated plasma analyzed immediately for glucose and lactate using immobilized enzyme chemistries (glucose oxidase, L-lactate oxidase, Analyzer model 2300-STAT, YSI, Yellow Springs, Ohio). The packed red cells were reinfused to minimize loss of red cell mass.

Plasma was collected for insulin measurement every 2 hours. Insulin was determined by radioimmunoassay (Micromedic human insulin RIA kit, ICN Biomedicals, Horsham, Pa.) with a sensitivity of 6 pM and a cross-reactivity to rat insulin of 89.5%.

Figure 10:
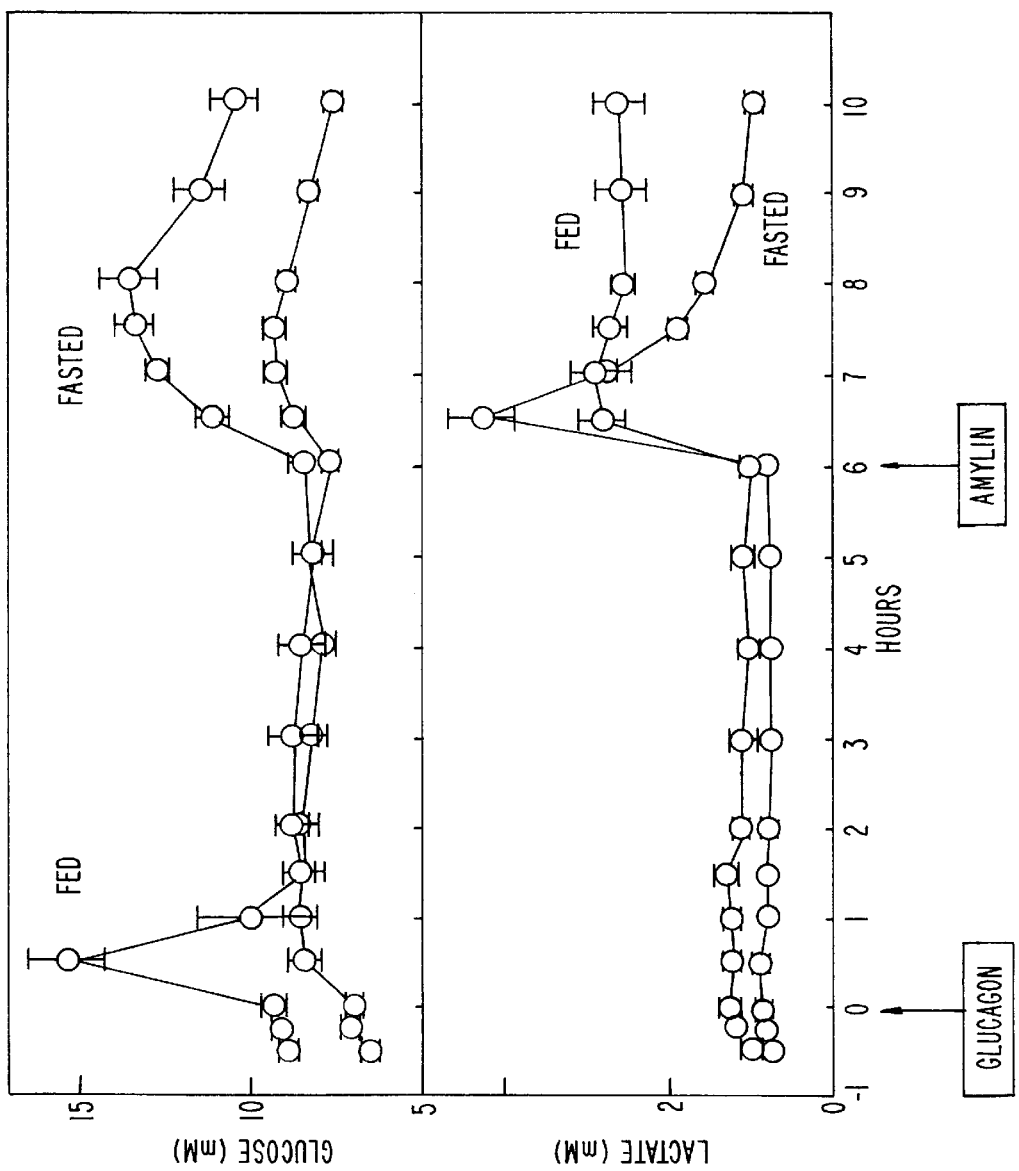
FIG. 10 shows the effects of an intravenous injection of 100 micrograms glucagon (0 hours) followed by an intravenous injection of 100 micrograms amylin (6 hours) on plasma arterial levels of glucose and lactate in (---O---) fed and (—O—) fasted (20±1 hour) rats.

In 20-hour fasted rats, glucagon injections resulted in a peak glycemic response of 1.94±0.34 mM which occurred 1.58±0.24 hours after i.v injection (see FIG. 10). The glycemic response to glucagon was less than that observed with either amylin alone (35% of that response, P<0.001) or with amylin subsequently injected into the same animals (35% of group 1 amylin response, P<0.003). Compared to control animals, there was no significant increment in plasma lactate with glucagon (0.09±0.04 mM; P=0.06). In the glucagon injected group, there was a significant elevation of mean arterial pressure (P<0.05) and heart rate (P<0.05) consistent with its reported inotropic and chronotropic effects.

Six hours after glucagon injection into fasted rats, amylin resulted in an increase in plasma glucose of 5.60±0.86 mM above the prevailing levels of 8.37±0.48 mN, peaking 1.67±0.27 hours post-injection, almost identical to the pattern observed with amylin alone. There was also a brisk lactate response of 3.44±0.42 mM (3.4 times greater than in amylin alone) the decline in amylin-generated lactate in the fasted group was 34 minutes. There were effects on arterial pressure similar to those observed in rats injected with amylin alone.

In contrast to the fasted animals (group 1), fed animals showed a brisk glycemic response to intravenous glucagon (see FIG. 10). The increment in plasma glucose was 6.29±0.92 mM above preinjection levels. However, compared to the more prolonged hyperglycemia produced by amylin, the glycemic response to glucagon relative to controls lasted only 0.6 hr. As in fasted animals (group 1), glucagon was not associated with a significant increase in plasma lactate (30 minute increment 0.07±0.08 mM, ns).

Amylin administered 6 hours later into these same fed rats resulted in a lactemic response 56% of that produced in fasted rats (lactate increment 1.92±0.22 mM, group 2 vs. group 1, P<0.05). The increase in plasma glucose was diminished compared to that observed in fasted rats (2-hour glucose increment 1.76±0.37 mM, group 2 response=31% group 1 response, p<0.01). The plasma lactate remained higher for longer in the fed rats (t½=138 min.) compared to the fasted rats. Plasma insulin levels for groups 1 and 2 are compared in Table 1. Levels were approximately 5 times higher in the fed animals than in the fasted animals.

TABLE 1

Insulin Levels (pM) in Fasted and Fed Rats

| Time (hours) | Fasted (group 1) | Fed (group 2) | p |
| --- | --- | --- | --- |
| 0 (pre-glucagon) | 46.2 ± 3.6 | 279.6 ± 94.8 | <0.03 |
| 2 | 43.8 ± 4.2 | 232.8 ± 65.4 | <0.01 |
| 4 | 58.8 ± 9.0 | 310.8 ± 48.0 | <0.001 |
| 6 (pre-amylin) | 45.0 ± 2.4 | 197.4 ± 19.2 | <0.001 |

EXAMPLE 5

In this example, amylin agonist activity in a soleus muscle-based assay (Leighton, B. and Cooper, G. J. S., Nature 335:632–635 (1988)) was measured.

Results are reported in Table 2.

TABLE 2

ACTIVITY OF AMYLIN AGONISTS

| Peptide | $EC_{50}$ in Soleus Muscle Assay |
| --- | --- |
| cyclo$^{2,7}$ [Asp$^2$,Lys$^7$]-Human Amylin | 22.96 nM ± 0.18 log unit |
| [Pro$^{29}$]-Human Amylin | 11 nM ± 0.10 log unit |
| [Leu$^{23}$]-Human Amylin | 94.48 nM ± 0.19 log unit |

EXAMPLE 6

In the further experiments set forth below, rat amylin was injected into rats subject to neither hyperinsulinemic nor somatostatin "clamp" in order to assess its actions in the presence of intact hormonal regulatory responses. Plasma glucose and lactate levels as well as blood pressure were monitored following intravenous injection of a range of doses of amylin into fasted animals, and also observed were the responses to subcutaneous injections. A study of amylin responses in fed animals is also set forth, as is a further comparison of the responses to amylin and glucagon in the fasted and fed anaesthetized rat.

Animals. Fifty two male Harlan Sprague Dawley rats were housed at 22.7±0.8° C. in a 12:12 hour light-dark cycle (experiments being performed during the light cycle) and fed and watered ad libitum (Diet LM-485, Teklad, Madison, Wis.). Fasted animals were deprived of food 20±1 hours prior to experimentation. Fed animals were allowed access to food until surgery.

Surgery/Instrumentation. Anesthesia was induced with 5% halothane, maintained at 2% during surgery and at 0.8–1% during metabolic recordings. Tracheotomy and cannulation of the right femoral artery and saphenous vein were performed.

The femoral arterial line was connected to a pressure transducer (Spectramed P23XL transducer, Model 13-4615-58 amplifier, Gould, Cleveland, Ohio) and perfused with heparinized saline (2 U/mL) at 3.0 ml/hr. All chronically infused agents were added to this infusate. The venous line was used for acute (bolus) injections.

A 4-limb ECG was monitored via an ECG/biotach amplifier (Model 13-4615-65A, Gould, Cleveland, Ohio) and heart rate derived.

Colonic temperature was measured using a thermistor probe and controller (Model 73A, YSI, Yellow Springs, Ohio) which provided closed-loop control of core temperature by switching a heated operating table.

Signals for heart rate, arterial pressure and colonic temperature were periodically sampled and stored with 12-bit precision at 20 Hz using a computerized data acquisition system (DT2801A A/D converters, DataTranslation, Marlboro, Mass.; AST Premium 386 computer, AST Research, Irvine, Calif.; Labtech Notebook software, Laboratory Technologies Corp., Wilmington, Mass.).

Treatment Groups.
1. Amylin Bolus (See FIG. 11) (n=6; mass-310±7 g; age=110±2 d; fasted with a 100 μl bolus of saline containing 76.8 nmol/kg freshly dissolved rat amylin having the 2Cys-7Cys S-S bond and C-terminal amidation required for full biologic activity (lot#ZG485, Bachem, Torrance, Calif.). Bioactivity of commercially available amylins (as measured by $EC_{50}$ of inhibition of insulin-stimulated glycogen synthesis in the isolated rat soleus muscle (18) may vary 100-fold (Cooper, G. J. S., et al., submitted). Therefore, the activity of peptide to be used in this study was first verified using the soleus muscle-based assay ($EC_{50}$=6.7±1.5 nM).

2. Subcutaneous Injections (See FIG. 12) (n=2; mass=333, 334 g; ages 92, 93 d; fasted 21:15, 19:50 hr:min). These animals were cannulated as all others, but at 2 hours after surgery received 100 μg amylin in 0.1 mL saline by subcutaneous rather than intravenous injection.

3. Dose Response Group (See FIG. 13) (n=26). These animals were treated similarly to those in group 1, except that data were collected for only 2 hours after injection and the dose of amylin was varied as follows: 0 μg amylin (n=3; mass=354±17 g; age=81±1 d; fasted 19.5±0.7 hr) 0.01 μg amylin (n=3; mass=379±5 g; age=78±1 d; fasted 20±0.5 hr) 0.1 μg amylin (n=3; mass=336±9 g; age=89±1 d; fasted 19.1±1.2 hr) 1 μg amylin (n=3; mass=341±10 g; age=85±0.3 d; fasted 20.8±1.8 hr) 10 μg amylin (n=4; mass=356±13 g; age=80±3 d; fasted 20.6±1.1 hr); 100 μg amylin (n=7; mass=310±7 g; age=110±2 d; fasted 20±0.7 hr) 1000 μg amylin (n=3; mass=314±7 g; age=81±0.3 d; fasted 22.7±1.8 hr).

Chemical Analyses. Arterial samples were drawn 0.5, 0.25 and 0 hr. before injection, and after injection at 0.5, 1, 1.5, 2 hrs. (group 3), at 3, 4, 5, 6 hrs. (groups 1 and 2), and at 6.5, 7, 7.5, 8, 9 and 10 hrs. (groups 4, 5 and 6). Arterial samples were collected into heparinized capillaries and the separated plasma analyzed immediately for glucose and lactate using immobilized enzyme chemistries (glucose oxidase, L-lactate oxidase, Analyzer model 2300-STAT, YSI, Yellow Springs, Ohio). The packed red cells were reinfused to minimize loss of red cell mass.

Plasma was collected for insulin measurement every 2 hours. Insulin was determined by radioimmunoassay (Micromedic human insulin RIA kit, ICN Biomedicals, Horsham, Pa.) with a sensitivity of 6 pM and a cross-reactivity to rat insulin of 89.5%.

Numerical Methods. Pairwise statistical analyses used Student's t-test routines (pooled variances methods) contained in the SYSTAT system (Systat, Evanson, Ill.). Unless stated otherwise, all results are reported as means ± standard error of the mean and P<0.05 is used as the level of significance.

Exponential decays were fitted to a single_component model (Y=A.e-kt+B) by non-linear regression analysis using routines containing in the NONLIN module of SYSTAT.

Sigmoid dose-response analyses used a least-squares iterative routine to fit a 4-parameter logistic function:

$$Y = \frac{A - D}{1 + (X/C)^{\wedge}B} + D$$

where A is the maximal response, D is basal, C is the $ED_{50}$, an dB is an exponent defining the steepness of the curve.

Intravenous Injections of amylin into Fasted Animals

Figure 11A:
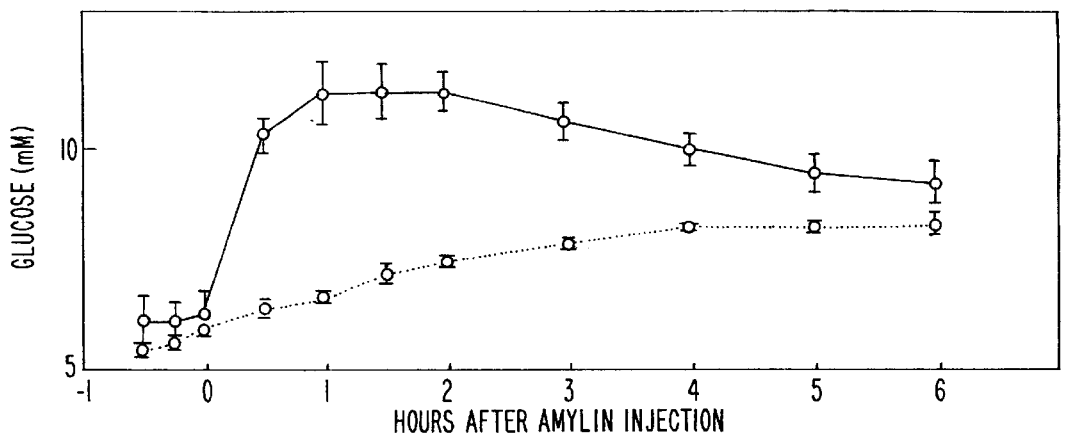
FIGS. 11A, 11B and 11C. Glycemic/lactemic/blood pressure responses to i.v. amylin. Plasma glucose (upper panel), plasma lactate (middle panel) and mean arterial pressure (lower panel) following intravenous injection of 25.5 nmol rat amylin (__) or saline (...), n=6 each. Symbols represent the mean±SEM.
Figure 11B:
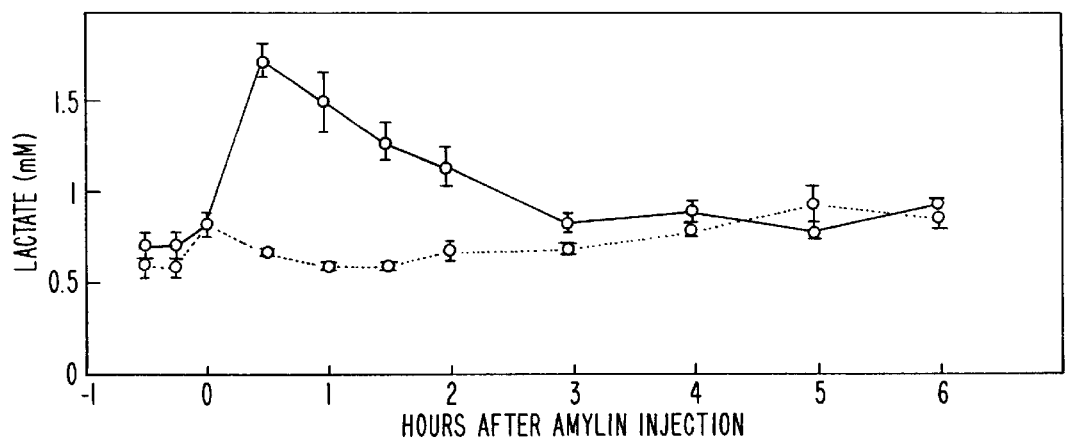
Figure 11C:
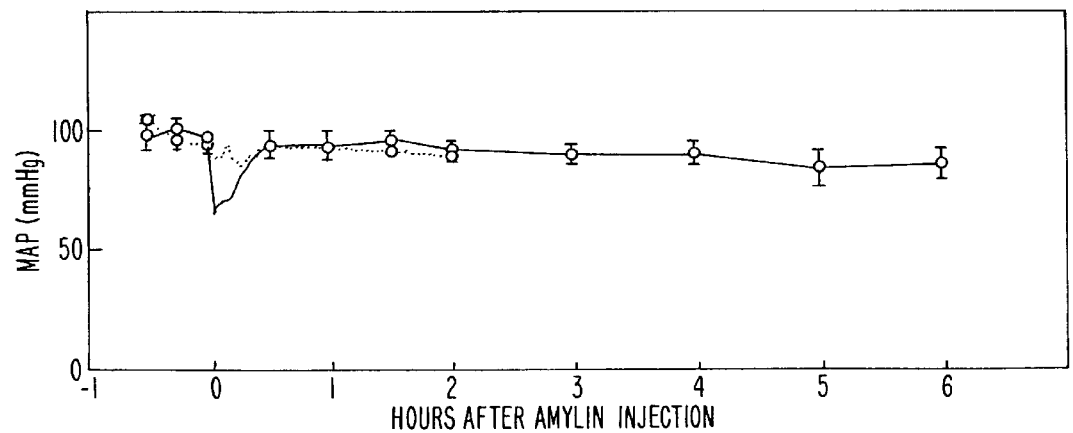

FIG. 11 shows a response to intravenous injection of a large amount, 100 μg, of amylin, approximately the amount estimated to be secreted by the rat pancreas in 24 hours. There is a rapid and transient fall in blood pressure consistent with the previously reported vasolidator action of the peptide. However, blood pressure is restored to control values within 30 minutes. There was a 2.4 fold increase in plasma lactate peaking at 1.7 mM at 30 minutes; plasma lactate returned to control levels by 3 hours. The results show that this response preceded the hyperglycemic response in which plasma glucose increased from 6.2 mM to a plateau of 11.8 mM, during the hour post-injection and then declined slowly to control values over the following 4 hours.

Sub-cutaneous Injection of amylin into Fasted Animals

An intravenous bolus of amylin gives an extremely high initial amylin plasma and extracellular fluid concentration, which could be responsible for the transient drop in blood pressure. The effects of the same dose, 100 μg, of amylin injected subcutaneously were therefore evaluated. As can be seen in FIG. 12, marked hyperlactemic and hyperglycemic effects are still present with the expected somewhat delayed time courses, lactate peaking at 1 to 1½ hours and glucose at 2 hours. Importantly, there was no significant effect on blood pressure indicating that the lactate response was independent of altered blood flows and blood pressure, and rather was a direct consequence of amylin action, presumably on skeletal muscle.

Dose-Response Relations

FIG. 13 shows the mean increments over control for glucose and lactate 30 minutes following i.v. injections of the indicated amounts of amylin. Also shown are the one minute decreases in blood pressure (which are near the nadir seen with this protocol). There is a discernible hyperglycemic effect and a clearly significant (P<0.05) hyperlactemic effect with an injection of 0.1 μg amylin, and significant elevations in both variables with an injection of 1 μg. There was no blood pressure change at doses less than 10 μg, so that injections of small doses of amylin produce metabolic effects without measurable changes in blood pressure. From the weight of the animals (310 g) and the proportion of body weight occupied by plasma and interstitial fluid (approximately 25%) (i.e. the extracellular fluid) it can be calculated that the amylin extracellular concentration, i.e. that relevant to cell surface receptors, could have peaked at no more than 300 pM (even assuming no binding, no sequestration of the cells, no degradation, and no excretion).

The hyperglycemic response has been fitted to a logistic function which has a slope of 0.61 and an ED 50 of 5.7 μg. See Table 3. The lactate response can not readily be fitted to such a function as there is no evidence of a plateau even with 1 mg injected amylin. It is believed that this reflects the hyperlactemic effect of the marked hypotension seen at these high amylin doses and is, in effect, a second phase of response reflecting amylin interactions at CGRP vascular receptors.

TABLE 3

Amylin Dose/Response Parameters

| | A (max resp) | B (slope) | C (ED50) | D (basal) |
|---|---|---|---|---|
| Glucose | 4.72 mM | −0.614 | 5.71 μg | 6.34 mM |
| Lactate | 2.30 mM | −0.243 | 181.6 μg | 0.75 mM |
| Arterial Pressure | 44.4 mmHg | 0.925 | 33.8 μg | 92.2 mmHg |

Parameters for best-fitting logistic functions for amylin dose vs arterial plasma glucose, lactate (30 minutes post-injection) and mean arterial pressure (1 minute post-injection).

EXAMPLE 7

We measured the effects of $hCGRP_{8-37}$ as an antagonist in two models of amylin action on glucose metabolism, the amylin-treated isolated stripped soleus muscle of the rat, and the amylin-injected 18-hr fasted normal rat in vivo. In addition, we observed its effect upon amylin-induced changes in blood pressure.

Animals. Harlan Sprague Dawley rats (332±9 g males, age 93±5 days), were housed at 22.7±0.8° C. in a 12:12 hour light:dark cycle (experiments being performed during the light cycle) and fed and watered ad libitum (Diet LM-485, Teklad, Madison, Wis.). Animals were fasted for 4 hours before isolation of soleus muscles, and 20±0.5 hours before in vivo experiments.

Chemicals. Soluble insulin, (Humulin-R, 100 U/ml) was purchased from Eli Lilly & Co., Indianapolis, Ind.. The conversion factor between activity units, U, and molar units for insulin used in the present study was 1 μU/ml=7.1 pM. HCGRP$_{8-37}$ (Lot #ZH201) was from Bachem (Torrance, Calif.). Chemical identity and purity of this peptide was determined as being about 98% by amino acid analysis, gas phase protein sequencing, and FAB mass spectrometry. The activity of rat amylin used in this study (lot #ZG485, Bachem) was measured at EC$_{50}$ 6.7±1.5 nM. Stock solutions of rat amylin and hCGRP$_{8-37}$ were prepared fresh daily in 150 mM NaCl. Concentrations of amylin and hCGRP$_{8-37}$ in protein-free stock solutions were verified using quantitative amino acid analysis. [U-$^{14}$C]-glucose (12.6 GBq/mmol) was purchased from New England Nuclear (Wilmington, Del). All other reagents were of analytical grade or better.

Isolation and incubation of stripped rat soleus muscles in the presence of various concentrations of insulin, amylin and hCGRP$_{8-37}$, and determination of rates of radioglucose incorporation into glycogen, were performed according to previously described methods. Leighton, B., and Cooper, G. J. S., Nature 335:632–635 (1988); Cooper, G. J. S., et al., Proc. Nat. Acad. Sci. USA, 85:7763–7766 (1988). Muscles were pre-incubated in Erlenmeyer flasks containing 10 mL Krebs-Ringer bicarbonate buffer at 37° C. with the following composition (in mM): NaCl, 118.5; NaHCO$_3$, 25; KCl, 5.94; CaCl$_2$, 2.54; KH$_2$PO$_4$, 1.19; MgSO$_4$, 1.19; D-glucose, 5.5; pH 7.40. Flasks were gassed continuously with O$_2$:CO$_2$ (95:5 vol/vol). After preincubation of muscles in this medium for 30 min at 37° C. in an oscillating water bath, muscle strips were transferred to similar vials containing the same medium with added [U-$^{14}$C] glucose (at 0.5 μCi/ml), human insulin (7.1 nM), rat amylin (100 nM), and increasing concentrations of hCGRP$_{8-37}$ (0, 1, 10, 100, 1000, 1×10$^4$, 3×10$^4$, 1×10$^5$ nM) (FIG. 14). Muscles were incubated for a further 60 minutes, then blotted, and [U-$^{14}$C] glucose incorporation into glycogen measured. Four muscle strips were incubated at each treatment condition, and each experiment was repeated three times.

Surgery and instrumentation. Anaesthesia was induced in 18-hr fasted rats using 5% halothane which was then maintained at 2% during surgery and at 0.8–1% during subsequent metabolic recordings. Tracheotomy and cannulation of right femoral artery and vein were performed and core temperature controlled with a thermoregulator (Model 73A, YSI, Yellow Springs, Ohio) which switched a heated operating table.

The femoral arterial line was connected to a pressure transducer (Spectramed P23XL transducer, Model 13-4615-58 amplifier, Gould, Cleveland, Ohio) and perfused with heparinized saline (2 U/ml) at 3.0 ml/hr. The femoral venous line was used for acute (bolus) injections, and hCGRP$_{8-37}$ was added to this infusate for chronic administration.

Signals for arterial pressure were sampled and stored with 12-bit precision at 20 Hz using a computerized data acquisition system (DT2801A A/D converters, DataTranslation, Marlboro, Mass.; AST Premium 386 computer, AST Research, Irvine, Calif.; Labtech Notebook software, Laboratory Technologies Corp., Wilmington, Mass.).

Treatment groups. There were three treatment groups. These were: (1) Amylin Bolus (n=7): After an initial 2 hr infusion, animals received 100 μL i.v. saline containing 25.5 nmol freshly dissolved rat amylin. (2) hCGRP$_{8-37}$ Primed Continuous Infusion with Amylin Bolus (n=3): Animals were injected at t=−30 min. with a 160 nmol bolus of hCGRP$_{8-37}$, followed by a continuous infusion of this peptide at 1.6 μmol/hr for 2 hr, then at 320 nmol/hr for a further hour, the total hCGRP$_{8-37}$ delivered being 3.7 μmol/rat=11.1 μmol/kg. At t=o min, animals received 100 μL i.v. saline containing 25.5 nmol fresh rat amylin as in (1) above. (3) Saline Controls (n=7): Instead of fresh amylin, rats were injected with 100 μL of saline vehicle.

Arterial samples were drawn 0.5, 0.25 and 0 hr before, and 0.5, 1, 1.5, 2, 3, and 4 hr after bolus injection. Samples were collected into heparinized capillaries and separated plasma was analyzed for glucose and lactate. Glucose and lactate were analyzed by immobilized enzyme chemistries (glucose oxidase, L-lactate oxidase, Analyzer model 23-STAT, YSI, Yellow Springs, Ohio).

Statistical analysis was performed using the non-paired, two-tailed Student's t-test (pooled variances method), using routines contained in the SYSTAT system (Systat, Evanston, Ill.), with levels of significance as stated. Results are reported as means ± s.e.m. Sigmoid dose-response analyses, from which EC$_{50}$ values were derived, used a least-squares iterative routine to fit a 4-parameter logistic function. DeLean, A., et al., ALLFIT Computer Program (NIH, Bethesda, Md. 20892).

In accord with the above Examples 2, 3, 4 and 6, amylin increased plasma lactate and plasma glucose, and decreased arterial pressure. Human CGRP$_{8-37}$ antagonized the effect of amylin to decrease glucose incorporation into skeletal muscle glycogen in vitro (FIGS. 14 and 15), and completely prevented amylin-induced elevations in plasma lactate and glucose levels in vivo (FIG. 16). It also prevented amylin-induced falls in arterial pressure (data not shown).

The effect of hCGRP$_{8-37}$ to antagonize the effect of amylin to inhibit insulin-stimulated incorporation of glucose into glycogen was measured in rat skeletal muscle in vitro (FIG. 14). Insulin (7.1 nM) increased rates of glucose incorporated into muscle glycogen 3.4-fold, from 0.83 (±0.08) to 2.84 (±0.22) μmol/g.hr; this effect was completely reversed by rat amylin (100 nM) so that rates of radioglucose incorporation into glycogen were not different between control (zero insulin/zero amylin) and maximal hormone conditions (insulin 7.1 nM/ amylin 100 nM). hCGRP$_{8-37}$ reversed in a dose-dependent manner, the amylin-mediated suppression of insulin-stimulated glucose incorporation, restoring the full, insulin response with an EC$_{50}$ of 5.92 μM (±0.13 log units) (FIG. 15). 100 μM hCGRP$_{8-37}$ completely eliminated the effect of 100 nM amylin on glucose incorporation, but had no measurable effect when administered alone (results not shown).

The ability of the antagonist hCGRP$_{8-37}$ to modify amylin's actions on carbohydrate metabolism, blood pressure and plasma calcium levels in fasted anaesthetized rats in vivo was also evaluated (FIG. 16). As shown in Example 6 above, amylin exerts dose-dependent effects to elevate blood levels of lactate and glucose when injected into normal rats. When amylin (66 nmol/kg) is injected into 18-hr fasted, normal rats, there is a rapid rise in blood lactate levels followed by an increase in blood glucose levels. The increase in glucose levels are partially due to increased endogenous glucose production which is believed to result from gluconeogenesis fueled by lactate released from muscle following amylin-activation of glycogen phosphorylase. These effects of amylin are independent of changes in levels of catecholamines, glucagon or insulin, and are not explained by the rapid changes in arterial pressure invoked by amylin or to the slower amylin-induced changes in calcium, since EDTA induced hypocalcemia does not change plasma glucose. Yamaguchi, M. and Yamamoto, T., Chem. Pharm. Bull. 25:2189–2194 (1977). In the present Example, after treatment of rats with $hCGRP_{8-37}$, blood levels of lactate and glucose following amylin administration did not differ from control animals (saline alone); that is, $hCGRP_{8-37}$ completely antagonized the effects of amylin to elevate blood levels of lactate or glucose.

Although the invention has been described with respect to specific embodiments, uses and methods, it will be appreciated that various changes and modifications may be made without departing from the invention.

We claim:

1. An assay method for use in identifying a test compound which can simulate the activity of amylin which method comprises:

a. bringing together a test sample and a test system, said test sample comprising one or more test compounds, and said test system comprising an in vivo biological model, said in vivo model being characterized in that it exhibits elevated lactate and elevated glucose in response to the introduction to said model of amylin or an amylin agonist;

b. determining the presence or amount of a rise in lactate and the presence or amount of a rise in glucose in said test system;

c. determining whether a peak in elevated lactate preceded a peak in elevated glucose; and d. identifying those test compounds which resulted in a peak in elevated lactate which preceded a peak in elevated glucose in the in vivo biological model in which at least one test compound in the test sample brought together with the test system results in a peak in elevated lactate which precedes a peak in elevated glucose.

2. The method of claim 1 which further comprises the use of a positive control assay, a negative control assay, or both.

3. The method of claim 2 wherein said positive control assay is carried out according to the method of claim 1 and said test sample comprises amylin or an amylin agonist.

4. The method of claim 1 wherein said in vivo model is a rat.

5. The method of claim 4 wherein said method is carried out using more than one rat, said rats being fed, or fasted, or both.

6. An assay method for use in evaluating the potency of a test compound known or suspected to simulate the activity of amylin, which method comprises:

a. bringing together a test sample and a test system, said test sample comprising one or more test compounds, and said test system comprising an in vivo biological model, said in vivo model being characterized in that it exhibits elevated lactate and elevated glucose in response to the introduction to said model of amylin or an amylin agonist;

b. determining the presence or amount of a rise in lactate and the presence or amount of a rise in glucose in said test system;

c. determining whether a peak in elevated lactate preceded a peak in elevated glucose; and d. evaluating the potency of those test compounds which resulted in a peak in elevated lactate which preceded a peak in elevated glucose in the in vivo biological model in which at least one test compound in the test sample brought together with the test system results in a peak in elevated lactate which precedes a peak in elevated glucose.

7. The method of claim 6, which further comprises the steps of repeating said assay method using differing amounts of said test sample, and generating a dose response profile for said rise in lactate for use in evaluating the potency of said test sample in simulating the activity of amylin.

8. The method of claim 6, which further comprises the steps of repeating said assay method using differing amounts of said test sample, and generating a dose response profile for said rise in glucose for use in evaluating the potency of said test sample in simulating the activity of amylin.

9. The method of claim 6, which further comprises the steps of repeating said assay method using differing amounts of said test sample, and generating a dose response profile for said rise in glucose and for said rise in lactate for use in evaluating the potency of said test sample in simulating the activity of amylin.

10. The method of claim 7, which further comprises comparing said dose response profile for said test sample to a dose response profile for said test sample to a dose response profile prepared for one or more positive control assays, or one or more negative control assays, or both, and evaluating the potency of said test sample in simulating the activity of amylin.

11. The method of claim 8, which further comprises comparing said dose response profile for said test sample to a dose response profile for said test sample to a dose response profile prepared for one or more positive control assays, or one or more negative control assays, or both, and evaluating the potency of said test sample in simulating the activity of amylin.

12. The method of claim 9, which further comprises comparing said dose response profile for said test sample to a dose response profile prepared for one or more positive control assays, or one or more negative control assays, or both, and evaluating the potency of said test sample in simulating the activity of amylin.

* * * * *